United States Patent
Caggiano et al.

(10) Patent No.: US 8,236,302 B2
(45) Date of Patent: Aug. 7, 2012

(54) COMPOSITIONS AND METHODS OF USING CHONDROITINASE ABCI MUTANTS

(75) Inventors: Anthony O. Caggiano, Larchmont, NY (US); Jennifer Iaci, Boonton, NJ (US); Andrea Vecchione, Mt. Vernon, NY (US); Elizabeth Markensohn, Flanders, NJ (US)

(73) Assignee: Acorda Therapeutics, Inc., Ardsley, NY (US)

( * ) Notice: Subject to any disclaimer, the term of this patent is extended or adjusted under 35 U.S.C. 154(b) by 259 days.

(21) Appl. No.: 12/757,006

(22) Filed: Jun. 4, 2010

(65) Prior Publication Data

US 2010/0239557 A1  Sep. 23, 2010

Related U.S. Application Data

(60) Continuation of application No. 12/338,207, filed on Dec. 18, 2008, now Pat. No. 7,731,956, which is a division of application No. 11/527,318, filed on Sep. 26, 2006, now Pat. No. 7,485,295.

(60) Provisional application No. 60/720,628, filed on Sep. 26, 2005.

(51) Int. Cl.
| | |
|---|---|
| A61K 38/00 | (2006.01) |
| A61K 38/46 | (2006.01) |
| C12N 9/88 | (2006.01) |
| C12N 9/24 | (2006.01) |
| C12Q 1/34 | (2006.01) |
| C07H 21/04 | (2006.01) |
| C07K 1/00 | (2006.01) |

(52) U.S. Cl. .................. 424/94.5; 424/94.62; 435/232; 435/200; 435/18; 536/23.2; 530/350

(58) Field of Classification Search .................. 424/94.5, 424/94.62; 435/232, 200, 18; 536/23.2; 530/350
See application file for complete search history.

(56) References Cited

U.S. PATENT DOCUMENTS

| | | | |
|---|---|---|---|
| 5,262,522 A | 11/1993 | Gearing | |
| 5,270,194 A | 12/1993 | D'Alterio et al. | |
| 5,496,718 A | 3/1996 | Hashimoto | |
| 5,498,536 A | 3/1996 | Khandke | |
| 5,578,480 A | 11/1996 | Khandke | |
| 5,652,122 A | 7/1997 | Frankel et al. | |
| 5,670,617 A | 9/1997 | Frankel et al. | |
| 5,674,980 A | 10/1997 | Frankel et al. | |
| 5,747,641 A | 5/1998 | Frankel et al. | |
| 5,763,205 A | 6/1998 | Hashimoto et al. | |
| 5,792,743 A | 8/1998 | Schachner | |
| 5,804,604 A | 9/1998 | Frankel et al. | |
| 5,869,301 A | 2/1999 | Nghiem et al. | |
| 5,997,863 A | 12/1999 | Zimmermann et al. | |
| 6,007,810 A | 12/1999 | Ishikawa | |
| 6,063,378 A | 5/2000 | Nohara et al. | |
| 6,093,563 A | 7/2000 | Bennett et al. | |
| 6,153,187 A | 11/2000 | Yacoby-Zeevi | |
| 6,171,575 B1 | 1/2001 | Okuyama | |
| 6,184,023 B1 | 2/2001 | Hashimoto et al. | |
| 6,200,564 B1 | 3/2001 | Lamont et al. | |
| 6,248,562 B1 | 6/2001 | Dunn et al. | |
| 6,313,265 B1 | 11/2001 | Phillips et al. | |
| 6,326,166 B1 | 12/2001 | Pomerantz et al. | |
| 6,972,168 B2 | 12/2005 | Muir et al. | |
| 7,008,783 B1 | 3/2006 | Sato et al. | |
| 7,074,581 B2 | 7/2006 | Yamashita et al. | |
| 7,163,545 B2 | 1/2007 | Yaszemski et al. | |
| 7,465,705 B2 | 12/2008 | Lee et al. | |
| 7,507,570 B2 | 3/2009 | Prabhakar et al. | |
| 7,560,106 B2 | 7/2009 | Sasisekharan et al. | |
| 2003/0040112 A1 | 2/2003 | Muir et al. | |
| 2003/0072749 A1 | 4/2003 | Muir et al. | |
| 2003/0077258 A1 | 4/2003 | Muir | |
| 2004/0033221 A1 | 2/2004 | Masuda et al. | |
| 2004/0265297 A1 | 12/2004 | Gruskin et al. | |
| 2005/0118157 A1 | 6/2005 | McMahon et al. | |
| 2005/0233419 A1 | 10/2005 | Pojasek et al. | |
| 2006/0078959 A1 | 4/2006 | Prabhakar et al. | |
| 2006/0153827 A1 | 7/2006 | Gruskin et al. | |
| 2006/0233782 A1 | 10/2006 | Gruskin et al. | |
| 2007/0104703 A1 | 5/2007 | Caggiano et al. | |
| 2007/0274979 A1 | 11/2007 | Gruskin et al. | |
| 2011/0250631 A1 | 10/2011 | Gruskin et al. | |
| 2011/0262413 A1 | 10/2011 | Gruskin et al. | |

FOREIGN PATENT DOCUMENTS

| | | |
|---|---|---|
| AU | 2003/208466 B2 | 9/2003 |
| AU | 2004/241088 A2 | 12/2004 |
| EP | 0704532 A2 | 3/1996 |
| EP | 1646353 A2 | 4/2006 |
| EP | 2353606 A2 | 8/2011 |
| EP | 2354155 A2 | 8/2011 |
| JP | H06-153947 | 6/1994 |
| JP | H10-174598 | 6/1998 |
| JP | H11-500308 | 1/1999 |
| JP | H11-236336 | 8/1999 |
| JP | 2002/505873 | 2/2002 |
| JP | 2002/526028 | 8/2002 |
| JP | 2003/500016 | 1/2003 |
| JP | 2004-89191 | 3/2004 |
| JP | 2004-113166 | 4/2004 |
| WO | WO 91/06303 A | 5/1991 |

(Continued)

OTHER PUBLICATIONS

Aldrich "Enzymer Explorer" 2009, URL:http://www.sigmaaldrich.com/life-science/metabolomics/enzyme-explorer/learning-center/carbohydrate-analysis/carbohydrate-analysis-iii.

(Continued)

*Primary Examiner* — Ganapathirama Raghu
(74) *Attorney, Agent, or Firm* — Pepper Hamilton LLP

(57) ABSTRACT

One aspect of the present invention relates to mutants of chondroitinase ABCI. Such chondroitinase ABCI mutants exhibit altered chondroitin lyase activity or increased resistance to inactivation from stressors including exposure to UV light or heat. Methods of using chondroitinase ABCI mutant enzymes are also provided.

13 Claims, 2 Drawing Sheets

FOREIGN PATENT DOCUMENTS

| | | |
|---|---|---|
| WO | WO 94/25567 A1 | 11/1994 |
| WO | WO 95/13091 A1 | 5/1995 |
| WO | WO 99/40787 A1 | 8/1999 |
| WO | WO 99/46368 A2 | 9/1999 |
| WO | WO 00/52149 A1 | 9/2000 |
| WO | WO 00/62067 A1 | 10/2000 |
| WO | WO 00/64482 A1 | 11/2000 |
| WO | WO 00/75319 A1 | 12/2000 |
| WO | WO 01/39795 A2 | 6/2001 |
| WO | WO 02/08285 A2 | 1/2002 |
| WO | WO 02/055684 A | 7/2002 |
| WO | WO 02/065136 A2 | 8/2002 |
| WO | WO 02/083179 A2 | 10/2002 |
| WO | WO 03/000901 A2 | 1/2003 |
| WO | WO 03/015612 A2 | 2/2003 |
| WO | WO 03/022882 A2 | 3/2003 |
| WO | WO 03/031578 A2 | 4/2003 |
| WO | WO 03/074080 A1 | 9/2003 |
| WO | WO 03/100031 A2 | 12/2003 |
| WO | WO 03/102160 A2 | 12/2003 |
| WO | WO 2004/017044 A2 | 2/2004 |
| WO | WO 2004/103299 A2 | 12/2004 |
| WO | WO 2004/110359 A2 | 12/2004 |
| WO | WO 2004/110360 A2 | 12/2004 |
| WO | WO 2005/087920 A2 | 9/2005 |
| WO | WO 2005/112986 A2 | 12/2005 |
| WO | WO 2007/038548 A2 | 4/2007 |

OTHER PUBLICATIONS

Anderson et al. "Tumor Cell Retention of Antibody Fab Fragments is Enhanced by an Attached HIV TAT Protein-Derived Peptide" 1993, *Biochem. & Biophys. Res. Commun.* 194(2):876-884.
Appel et al. "Several Extracellular Domains of the Neural Cell Adhesion Molecule L1 are Involved in Neurite Outgrowth and Cell Body Adhesion" 1993, *J. Neurosc.* 13(11): 4764-4775.
Avrameas et al. "Polyreactive anti-DNA monoclonal antibodies and a derived peptide as vectors for the intracytoplasmic and intranuclear translocation of macromolecules" 1998, *Proc. Natl. Acad. Sci. USA* 95:5601-5606.
Banker et al. "Modern Pharmaceutics" 2002, 4th Ed., *Informa Healthcare*, New York (TOC).
Bao et al. "A Functional Dermatan Sulfate Epitope Containing Iduronate (2-O-sulfate) α1-3GalNAC (6-O-sulfate) Disaccharide in the Mouse Brain" 2005, *J. of Bio. Chem.* 280(24):23184-23193.
Basso et al. "A Sensitive and Reliable Locomotor Rating Scale for Open Field Testing in Rats" 1995, *J. of Neurotrama* 12(1):1-21.
Bixby et al. "Neurite outgrowth on muscle cell surfaces involves extracellular matrix receptors as well as Ca2+-dependent and —independent cell adhesion molecules" 1987, *Proc. Natl. Acad. Sci. USA* 84:2555-2559.
Bowie et al. "Deciphering the Message in Protein Sequences: Tolerance to Amino Acid Substitutions" 1990, *Science* 247:1306-1319.
Bradbury et al. "Chondroitinase ABC Promotes Regeneration and Functional Recovery Following Spinal Cord Injury" 2001, *Soc. for Neuroscience Abstracts* 27(2):1835.
Bradbury et al. "NT-3 Promotes Growth of Lesioned Adult Rat Sens Ory Axons Ascending in the Dorsal Columns of the Spinal Cord" 1999, Eur. J. Neurosc. 11(11):3873-3783.
Bray et al., Neuronal and Nonneuronal Influences on Retinal Ganglion Cell Survival, Axonal Regrowth, and Connectivity after Axotomy, 1991, *Ann. NY Acad. Sci.*, 214-228.
Burgess et al. "Possible Dissassociation of the Heparin-binding and Mitogenic Activities of Heparin-binding (Acidic Fibroblast) Growth Factor-1 From its Receptor-binding Activities by Site-directed Mutagenesis of a Single Lysine Residue" 1990, *J. of Cell. Bio.* 111:2129-2138.
Cadelli et al. "Oligodendrocyte- and Myelin-Associated Inhibitors of Neurite Outgrowth: Their Involvement in the Lack of CNS Regeneration" 1992, *Exp. Neur.* 115:189-192.
Cajal "Degeneration & Regeneration of the Nervous System" May ed., 1959, *Hafner Publ. Co.*, New York (TOC).
Chang et al. "Extension of Neurites on Axons is Impaired by Antibodies against Specific Neural Cell Surface Glycoproteins" 1987, *J. Cell. Biol.* 104:355-362.
Chen et al. "Peripheral nerve regeneration using silicone rubber chambers filled with collagen, laminin and fibronectin" 2000, *Biomat.* 21:1541-1547.
Crespo et al. "How Does Chondroitinase Promote Functional Recovery in the Damaged CNS?" 2007, *Ex. Neurology* 206:159-171.
Curinga et al. "Mammalian-produced Chondroitinase AC Mitigates Axon Inhibition by Chondroitin Sulfate Proteoglycans" 2007, *J. of Neurochemistry* 102:275-288.
Daichi "Text Book of Physiology" 2000, 3rd Ed. 81.
Degrendele et al. "Requirement for CD44 in Activated T Cell Extravassation into an Inflammatory Site" 1997, *Science* 278:672-675.
Denuziere et al. "Chitosan-Chondroitin sulfate and chitosan-hyaluronate polyelectrolyte complexes: biological properties" 1998, *Biomaterials* 19:1275-1285.
Derossi et al. "Cell Internalization of the Third Helix of the Antennapedia Homeodomain is Receptorindependent" 1996, *J. Bioi. Chem* 271:18188-18193.
Doppenberg et al. "Clinical Trials in Traumatic Brain Injury" 1998, *Ann. NY Acad. Sci.* 305-319.
Edelman "Cell Adhesion Molecules" 1983, *Science* 219:450-457.
Edelman et al. "Morphoregulatory Molecules" 1990, *Wiley*, New York (TOC).
Efthymiadis et al. "The HIV-1 Tat Nuclear Localization Sequence Confers Novel Nuclear Import Properties" Jan. 16, 1998, *J. Biol. Chem.* 273(3):1623-1628.
Ellioit et al. "Intercellular Trafficking and Protein Delivery by a Herpesvirus Structural Protein" 1997, *Cell* 88:223-233.
Fahraeus et al. "Inhibition of pRb phosphorylation and cell-cycle progression by a 20-residue peptide derived from p16CDKN2IINK4A" 1996, *Curr. Biol.* 6(1):84-91.
Favre et al. "Hyaluronidase enhances recombinant adeno-associated virus (rAAV)-mediated gene transfer in the rat skeletal muscle" 2000, *Gene Ther.* 7(16):1417-1420.
Fawell et al. "Tat-mediated delivery of heterologous proteins into cells" 1994, *Proc. Natl. Acad. Sci. USA* 91:664-668.
Fethiere et al. "Crystal Structure of Chondroitin AC Lyase, a Representative of a family of Glycosaminoglycan Degrading Enzymes" 1999, *J. Mol. Biol.* 288:635-647.
Fongmoon et al. "Chondroitinase-mediated Degradation of Rare 3-)-Sulfated Glucuronic Acid in Functional Oversulfated Chondroitin Sulfate K and E" 2007, *J. of Bio. Chem.* 282(51):36895-39904.
Frankel et al. "Tat Protein from Human Immunodeficiency Virus Forms a Metal-Linked Dimer" 1988, *Science* 240:70-73.
Frankish et al. "Spinal-cord Repair Moves a Step Closer" 2002, *The Lancet* 359(9314):1317.
Gennaro "Remington's Pharmaceutical Sciences" 1985, *Mack Publishing Company* (PA) 17th Ed. (TOC).
Goodman et al. "The Pharmacological Basis of Therapeutics" 10th ed., 2001, *McGraw Hill*, New York (TOC).
Hiyama et al. "Crystallization and Some Properties of Chondroitinase from *Arthrobacter aurescens*" 1975, *J. Biol. Chem.* 250:1824-1828.
Hlavin et al. "Molecular Structure and Functional Testing of Human L1CAM: An Interspecies Comparison" 1991, *Genomics* 11:416-423.
Horstkorte et al. "The Fourth Immunoglobin-like Domain of NCAM Contains a Carbohydrate Recognition Domain for Oligomannosidic Glycans Implicated in Associated with L1 and Neurite Outgrowth" 1993, *J. Cell Biol.* 121(6):1409-1421.
Huang et al. "Active Site of Chondroitin AC Lyase Revealed by the Structure of Enzyme-Oligosaccharide Complexes and Mutagenesis" Jan. 1, 2001, *Biochemistry*, 40(8):2359-2372.
Huang et al. "Crystal Structure of Chondroitinase B from *Flavobacterium heparinum* and its Complex with a Disaccharide Product at 107 A Resolution" 1999, *J. Mol. Biol.* 294:1257-1269.
Iida et al. "Cell Surface Chondroitin Sulfate Proteoglycans in Tumor Cell Adhesion, Motility and Invastion" 1996, *Seminars in Cancer Biology* 7:155-162.
Iwai et al. "Axon Patterning Requires DN-cadherin, a Novel Neuronal Adhesion Receptor, in the *Drosphila* Embryonic CNS" 1997, *Neuron* 19:77-89.
Jones "Taking a new TAK on Tat transactivation" 1997, *Genes & Dev.* 11:2593-2599.

Jung et al. "Transit time of leutocytes rolling through venules controls cytokine-induced inflammatory cell recruitment in vivo" 1998, *J. Clin. Invest.* 102(8):1526-1533.

Kadmon et al. "Functional Cooperation between the Neural Adhesion Molecules L1 and N-CAM is Carbohydrate Dependent" 1990, *J. Cell Biol.* 110:209-218.

Kadmon et al. "The Neural Cell Adhesion Molecule N-CAM Enhances L1-dependent Cell-Cell Interactions" 1990, *J. Cell Biol.* 110:193-208.

Khan et al. "Animal Models of Spinal Cord Contusion Injuries", 1999, *Laboratory Animal Science* 49(2): 161-172.

Kim et al. "Insertion and Deletion Mutants of FokI Restriction Endonuclease" 1994, *J. Biol. Chem.* 269(50):31978-31982.

Kubota et al. "Functional Similarity of HIV-1 Rev and HTLV-1 Rex Proteins: Identification of a New Nucleolar-Targeting Signal in Rev Protein" Aug. 15, 1989, *Biochem. Biophys. Res. Commun.* 162(3):963-970.

Lagenaur et al. "An L1-like molecule, the 8D9 antigen, is a potent substrate for neurite extension" 1987, *Proc. Natl. Acad. Sci. USA* 84:7753-7757.

Lemons et al. "Chondroitin Sulfate Preteoglycan Immunoreactivity Increases Following Spinal Cord Injury and Transplantation" 1999, *Exper. Neurology* 160:51-65.

Lesley et al. "Variant Cell Lines Selected for Alterations in the Function of the Hyaluronan Receptor CD44 Show Differences in Glycosylation" 1995, *J. Exp. Med.* 182:431-437.

Li et al. "Delayed systemic Nogo-66 Receptor Antagonist Promotes Recovery from Spinal Cord Injury" 2003, *J. Neuroscience* 23(10):4219-4227.

Lindner et al. "L1 mono- and polyclonal antibodies modify cell migration in early postnatal mouse cerebellum" 1983, *Nature* 305:427-430.

Lodish et al. "Integrating cells into tissue" 2000, *Mol. Cell Biology*, 5th Ed., Chapter 6.

Mahanthappa et al. "Glial Growth Factor 2, a Soluble Neuregulin, Directly Increases Schwann Cell Motility and Indirectly Promotes Neurite Outgrowth" 1996, *J. Neuroscience* 16(15):4673-4683.

Maniatis et al. "Molecular Cloning: A Laboratory Manual" 1982, *Cold Spring Harbor Lab.* (TOC).

Mann et al. "Endocytosis and Targeting of Exogenous HIV-1 Tat Protein" Jul. 10, 1991, *EMBO J.* 10(7):1733-1739.

Martini et al. "Restricted Localization of L1 and N-CAM Sites of Contact Between Schwann Cells and Neurites in Culture" 1994, *GLIA* 10:70-74.

Matinysn "Restoration of functions due to Enzyme Therepy After Complete Transaction of the Spinal Cord" 1965, *Zh Ek Sp Klin Med* 5(3):3-13.

Matsumoto et al. "Peripheral nerve regeneration across an 80-mm gap bridged by a polyglycolic acid (PGA)-collagen tube filled with laminin-coated collagen fibers: a histilogical and electrophysiological evaluation of regenerated nerves" 2000, *Brain Res.* 868:315-328.

Matteuci et al. "Synthesis of Deoxyoligonucleotides on a Polymer Support" 1981, *J. Am. Chem. Soc.* 103:3185-3191.

McGee et al. "The Nogo-66 Receptor:Focusing Myelin Inhibition of Axon Regeneration" 2003, *Trends in Neuroscience* 26(4):193-198.

Michelacci et al. "Isolation and Partial Characterization of an Induced Chondroitinase β from *Flavobacterium heparium*" 1974, *Biochem. & Biophys. Res. Comm.* 56(4):973-980.

Miura et al. "Analysis of Glycosaminoglycan-Degrading Enzymes by Substrate Gel Electrophoresis (Zymography)" 1995, *Anal. Biochem.* 225:333-340.

Modena et al. "Hylauronidase-injectable microparticles intended for the treatment of extravasation" 1998, *J. Microencapsulation* 15(1):85-92.

Moon et al. "Regeneration of CNS axons back to their target following treatment of adult rat brain with chondroitinase ABC" 2001, *Nature Neurosc.* 4(5): 465-466.

Moos et al. "Neural adhesion molecule L1 as a member of the immunoglobulin superfamily with binding domains similar to fibronectin" 1988, *Nature* 334:701-703.

Nagahara et al. "Transduction of fUll-length TAT fusion proteins into mammalian cells: TAT_p27Klp1 induces cell migration" 1998, *Nat. Med.* 4(12):1449-1452.

Netti et al. "Role of Extracellular Matrix Assembly in Interstitial Transport in Solid Tumors" 2000, *Cancer Res.* 60(9):2497-2503.

Nieke et al. "Expression of the neural cell adhesion molecules L1 and N-CAM and their common carbohydrate epitope L2/HNK-1 during development and after transaction of the mouse sciatic nerve" 1985, *Differentiation* 30:141-151.

Oermann et al. "The Use of Anti-inflammatory Medications in Cystic Fibrosis" 1999, *Chest* 115:1053-1058.

Olmarker et al. "Chondroitinase ABC (Pharmaceutical Grade) for Chemonucleolysis" 1996, *Spine* 21(17):1952-1956.

Pawson et al. "Assembly of Cell Regulatory systems Through Protein Interaction Domains" 2003, *Science* 300:445-452.

Pillwein et al. "Hyaluronidase Additional to Standard Chemotherapy Improves Outcome for Children with Malignant Tumors" 1998, *Cancer Letters* 131:101-108.

Pojasek et al. "Biochemical Characterization of the Chondroitinase B Active Site" Aug. 23, 2002, *J. Biol. Chem.* 277(34):31179-31186.

Pojasek et al. "Recombinant Expression, Purification, and Kinetic Characterization of Chondroitinase AC and Chondroitinase B from *Flavobacterium heparinum*" 2001, *Biochem, Biophys. Res. Commun.* 286:343-351.

Prabhakar et al. "Biochemical Characterization of the Chondroitinase ABC I Active Site" Aug. 23, 2005, *Biochem. J.*, pp. 395-405.

Priestley et al. "Stimulating regeneration in the damaged spinal cord" 2002, *J. Phyl.* 96:123-133.

Rathjen et al. "Immunocytological and biochemical characterization of a new neuronal cell surface component (L1 antigen) which is involved in cell adhesion" 1984, *EMBO J.* 3(1):1-10.

Ratjen et al. "Cystic Fibrosis" 2003, *The Lancet* 361(9358):681-689.

Reich et al. "Small interfering RNA (siRNA) targeting VEGF effectively inhibits ocular neovascularization in a mouse model" 2003, *Molecular Vision* 9:210-216.

Reid et al. "Variants of Human L1 Cell Adhesion Molecule Arise through Alternate Splicing of RNA" 1992, *J. Mol. Neurosc.* 3:127-135.

Roy et al. "Generation of Substantially Smaller Deletion Mutants of Chondroitinase AC and B Those are Biologically Active" Nov. 8-12, 2003, Society for Neuroscience Abstract Viewer and Itinerary Planner, 33rd Annual Meeting of the Society of Neuroscience, New Orleans, LA, *Database Biosis*. (Abstract).

Saito et al. "Enzymatic Methods for the Determination of Small Quantities of Isomeric Chondroitin Sulfates" 1968, *J. Biol. Chem.* 243(7):1536-1542.

Sato, et al. "Subunit Structure of Chondroitinase ABC from *Proteus vulgaris*" 1986 *Agric. Biol. Chem.* 50(4):1057-1059.

Schachner "Functional implications of glial cell recognition molecules" 1990, *Neurosc.* 2:497-507.

Schwab "Nerve fibre regeneration after traumatic lesions of the CNS; progress and problems" 1991, *Phil. Trans. R. Soc. Lond.* 331:303-306.

Schwarze et al. "In Vivo Protein Transduction: Delivery of a Biologically Active Protein into the Mouse" 1999, *Science* 285:1569-1572.

Seikagaku Biobus. Corp. "Chondroitinase AC II pamphlet" 2009, URL:http/www.seikagakubb.co.jp/bio/cgi-bin/search/tenpu_pdf/100335.pdf.

Seilheimer et al. "Studies of Adhesion Molecules Mediating Interactions between Cells of Peripheral Nervous System Indicate a Major Role for L1 in Mediating Sensory Neuron Growth on Schwann Cells in Culture" 1988, *J. Cell Biol.* 107:341-351.

Silver et al. "Postnatally induced formation of the corpus callosum in acallosal mice on glia-coated cellulose bridges" 1983, *Science* 220:1067-1069.

Smiseth et al. "Effect of Hyaluronidase on Substrate Exchange and Blood Flow in the Ischaemic Myocardium of the Dog" 1982, *Clinical Physiology* 2(1):39-50.

Smith-Thomas et al. "Increased Axon Regeneration in Astrocytes Grown in the Presence of Proteoglycan Synthesis Inhibitors" 1995, *J. of Cell Science* 108(3):1307-1315.

Southern "Detection of Specific Sequences Among DNA Fragments Separated by Gel Electrophoresis" 1975, *J. Mol. Biol.* 98:503-517.

Stedman's Medical Dictionary 2000, Lippincott Williams & Wilkins, 27th Ed.

Sterne et al. "Neurotrophin-3 Delivered Locally via Fibronectin Mats Enhances Peripheral Nerve Regeneration" 1997, *Eur. J. Neurosc.* 9:1388-1396.

Tona et al. "Effect of Hyaluronidase on Brain Extracellular Matrix in Vivo and Optic Nerve Regeneration" 1993, *J. Neurosc. Res.* 36:191-199.

Trigg et al. "Peripheral Nerve Regeneration: Comparison of Laminin and Acidic Fibroblast Growth Factor" 1998, *Am. J. Otolaryngology* 19(1):29-32.

Tsuda et al. "Substrate Specificity Studies of *Flavobacterium* Chondroitinase C and Heparitinases Towards the Glycosaminoglycan-protein Linkage region" 1999, *European J. of Biochem.* 262:127-133.

Vives et al. "A Truncated HIV-1 Tat Protein Basic Domain Rapidly Translocates through the Plasma Membrane and Accumulates in the Cell Nucleus" 1997, *J. Biol. Chem.* 272(25):16010-16017.

Vives et al. "Effects of the Tat Basic Domain on Human Immunidefieciency Virus Type 1 Transactivation, Using Chemically Synthesized Tat Protein and Tat Peptides" May 1994, *J. Virol.* 68(5):3343-3353.

Williams et al. "Calcium Influx into Neurons Can Solely Account for Cell Contact-dependent Neurite Outgrowth Stimulated by Transfected L1" 1992, *J. Cell Biol.* 119(4):883-892.

Wood et al. "Inhibition of Schwann Cell Myelination in vitro by Antibody to the L1 Adhesion Molecule" 1990, *J. Neurosc.* 10(11):3635-3645.

Yamagata et al. "Repression of a Malignant Cell-Substratum Adhesion Phenotype by Inhibiting the Production of the Anti-Adhesive Proteoglycan, PG-M/Versican" 1994, *J. of Cell Science* 1007:2581-2590.

Yang et al. "Developmental Regulation of a Matrix Metalloproteinase during Regeneration of Axolotl Appendages" 1994, *Dev. Biol.* 166:696-703.

Yang et al. "Expression of Mmp-9 and Related Matrix Metalloproteinase Genes During Axolotl Limb Regeneration" 1999, *Dev. Dyn.* 216:2-9.

Yasuda et al. "Effect of Hyluronidase on Experimental Cerebral Infarct Size and Mortality" 1982, *Lab. Invest.* 46:400-404.

Yick et al. "Chondroitinase ABC promotes axonal regeneration of Clarke's neurons after spinal cord injury" 2000, *Regeneration and Transpl.* 11(5):1063-1067.

Yick et al. "Chondroitinase ABC Promotes Axonal Regrowth of Clarke's Neurons Into Peripheral Nerve Graft After Hemisection of the Spinal Cord" 1999, *Soc. for Neuroscience Abstracts* 25:747.

Fawcett et al., The Glial Scar and Central Nervous System Repair, 1999, Brain Res. Bull. 49(6):377-391.

Bradbury et al., Chondroitinase ABC Promotes Functional Recovery After Spinal Cord Injury, 2002, Nature 416:636-640.

Hoffman et al., Chondroitin Sulfates, 1958, Federation Proc. 17:1078-1082.

Yamagata et al., Purification and Properties of Bacterial Chondroitinases and Chondrosulfatases, 1968, J. Biol. Chem. 243(7):1523-1535.

Michelacci et al., Isolation and Characterization of an Induced Chondroitinase ABC from *Flavobacterium heparinum*, 1987, Biochem. Biophys. Acta 923:291-301.

Banker et al., Modern Pharmaceutics, 1979, Marcel Dekker, Inc., New York, New York, (TOC).

Goodman et al., The Pharmacological Basis of Therapeutics, $6^{th}$ ed. 1980, MacMillan Pub., New York, (TOC).

Michelacci et al., Chondroitinase C from *Flavobacterium heparinum*, 1976, J. Biol. Chem. 251(4):1154-1158.

Zuo et al., Degradation of Chondroitin Sulfate Proteoglycan Enhances the Neurite-Promoting Potential of Spinal Cord Tissue, 1998, Exp. Neurol. 154(2):654-662.

Zuo et al., Regeneration of Axons after Nerve Transection Repair is Enhanced by Degradation of Chondroitin Sulfate Proteoglycan, 2002, Exp. Neurol. 176(1):221-228.

Krekoski et al., Axonal Regeneration into Acellular Nerve Grafts is Enhanced by Degradation of Chondroitin Sulfate Proteoglycan, 2001, J. Neurosci. 21(16):6206-6213.

Blight, Animal Models of Spinal Cord Injury, 2002, Topics in Spinal Cord Injury Rehabilitation 6(2):1-13.

Kwon et al., Animal Models Used in Spinal Cord Regeneration Research, 2002, Spine 27(14):1504-1510.

Hirschberg et al., Inflammation after Axonal injury has Conflicting Consequences for Recovery of Function: Rescue of Spared Axons is Impaired but Regeneration is Supported, J. Neuroimmunol. 1994, 50(1):9-16(Abstract).

Hou et al., Endotoxin Removal by Anion-Exchange Polymeric Matrix, 1990, Biotech. Appl. Biochem. 12:315-324.

Hamai et al., Two Distinct Chondroitin Sulfate ABC Lyases, 1997, J. Biol. Chem. 272(14):9123-9130.

Broach et al., Experimental Manipulation of Gene Expression, M. Inouye ed., Academic Press, New York, 1983, pp. 83-117.

Sambrook et al., Molecular Cloning, $2^{nd}$ ed., Cold Spring Harbor Laboratory Press, New York, New York, 1989, Ch. 16 and 17.

Sambrook et al., Molecular Cloning, $2^{nd}$ ed., Cold Spring Harbor Laboratory Press, New York, New York, 1989 (TOC).

Ben-Bassat et al., Processing of the Initiation Methionine from Proteins: Properties of the *Escherichia coli* Methionine Aminopeptidase and its Gene Structure, 1987, J. Bacteriol. 169(2):751-757.

Miller et al., N-Terminal Methionine-Specific Peptidase in *Salmonella typhimurium*, 1987, PNAS 84:2718-2722.

Korn, 1957, The Degradation of Heparin by Bacterial Enzymes, J. Biol. Chem. 226:841-844.

Martinez et al., Purification and Properties of the Enzyme Chondroitinase, 1959, J. Biol. Chem. 234(9):2236-2239.

Huang et al., Crystal Structure of *Proteus vulgaris* Chondroitin Sulfate ABC Lyase I at 1.9 A Resolution, 2003, J. Mol. Biol. 328:623-634.

Michelacci et al., A Comparative Study Between a Chondroitinase B and a Chondroitinase AC from *Flavobacterium heparinum*, 1975, Biochem. J. 151:121-129.

Sato et al., Cloning and expression in *Escherichia coli* of the gene encoding the *Proteus vulgaris* chondroitin ABC lyase, 1994, Appl. Microbiol. Biotechnol. 41:39-46.

Caggiano et al., Chondroitinase ABCI Improves Locomotion and Bladder Function following Contusion Injury of the Rat Spinal Cord, 2005, J. Neurotrauma 22(2):226-239.

Accession P59807, Aug. 15, 2003.

Chau et al. "Chondroitinase ABC Enhances Axonal Regrowth Through Schwann Cell-seeded Guidance Channels After Spinal Cord Injury" Nov. 20, 2003 *FASEB J.* 18(1):1-24 (XP003008297).

Dimayuga et al. "The Neuregulin GGF2 Attenuates Free Radical Release from Activated Microglial Cells" Mar. 2003, *J. Neuroim.* 136(1-2):67-74 (XP002651543).

European Search Report for EP11152626 dated Jul. 21, 2011.

European Search Report for EP10184697 dated Jul. 12, 2011.

Grandpre et al. "Nogo-66 Receptor Antagonist Peptide Promotes Axonal Regeneration" May 30, 2002, *Nature* 417(6888):547-551 (XP002651544).

Hunt et al. "The Nogo Receptor, Its Ligands and Axonal Regeneration in the Spinal Cord; a Review" Feb. 2002, *J. Neurocytology* 31(2):93-120 (XP002651545).

Roy et al. "Treatment with Recombinant Chondroitinases AC and B Permits Neuronal Outgrowth Over Inhibitory Chondroitin Sulfate Proteoglycans (CSPGs)" Nov. 7, 2002, *Society for Neuroscience Abstract Archives* 2000-2005 (Abstract) (XP009150388).

SEQUENCE LISTING

```
<160> NUMBER OF SEQ ID NOS: 9

<210> SEQ ID NO 1
<211> LENGTH: 1027
<212> TYPE: PRT
<213> ORGANISM: Artificial
<220> FEATURE:
<223> OTHER INFORMATION: Chondroitinase ABCI

<400> SEQUENCE: 1
```

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285
```

```
Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Cys Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Gly Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
690                 695                 700

Glu Gly Gln Tyr Gly Met Met Ala Phe Asp Leu Ile Tyr Pro Ala Asn
```

```
                705                 710                 715                 720
Leu Glu Arg Phe Asp Pro Asn Phe Thr Ala Lys Lys Ser Val Leu Ala
                    725                 730                 735

Ala Asp Asn His Leu Ile Phe Ile Gly Ser Asn Ile Asn Ser Ser Asp
                740                 745                 750

Lys Asn Lys Asn Val Glu Thr Thr Leu Phe Gln His Ala Ile Thr Pro
                755                 760                 765

Thr Leu Asn Thr Leu Trp Ile Asn Gly Gln Lys Ile Glu Asn Met Pro
            770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
                820                 825                 830

Phe Ser Ser Ala Trp Ile Asp His Ser Thr Arg Pro Lys Asp Ala Ser
            835                 840                 845

Tyr Glu Tyr Met Val Phe Leu Asp Ala Thr Pro Glu Lys Met Gly Glu
        850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Ala Cys Arg Asp Ala Thr His Glu Arg Ala Pro
        995                 1000                1005

Glu Thr Ile Cys Ser Ile Asn Cys Cys Asn Phe Ile Asp Glu Asn
    1010                1015                1020

Thr Ile Ala Leu
    1025

<210> SEQ ID NO 2
<211> LENGTH: 1027
<212> TYPE: PRT
<213> ORGANISM: Artificial
<220> FEATURE:
<223> OTHER INFORMATION: Chondroitinase ABCI

<400> SEQUENCE: 2

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45
```

-continued

```
Gln Ser Leu Leu Trp Lys Trp Lys Gly Gly Ser Ser Phe Thr Leu His
     50                  55                  60
Lys Lys Leu Ile Val Pro Thr Asp Lys Glu Ala Ser Lys Ala Trp Gly
 65                  70                  75                  80
Arg Ser Ser Thr Pro Val Phe Ser Phe Trp Leu Tyr Asn Glu Lys Pro
                 85                  90                  95
Ile Asp Gly Tyr Leu Thr Ile Asp Phe Gly Glu Lys Leu Ile Ser Thr
            100                 105                 110
Ser Glu Ala Gln Ala Gly Phe Lys Val Lys Leu Asp Phe Thr Gly Trp
        115                 120                 125
Arg Thr Val Gly Val Ser Leu Asn Asn Asp Leu Glu Asn Arg Glu Met
    130                 135                 140
Thr Leu Asn Ala Thr Asn Thr Ser Ser Asp Gly Thr Gln Asp Ser Ile
145                 150                 155                 160
Gly Arg Ser Leu Gly Ala Lys Val Asp Ser Ile Arg Phe Lys Ala Pro
                165                 170                 175
Ser Asn Val Ser Gln Gly Glu Ile Tyr Ile Asp Arg Ile Met Phe Ser
            180                 185                 190
Val Asp Asp Ala Arg Tyr Gln Trp Ser Asp Tyr Gln Val Lys Thr Arg
        195                 200                 205
Leu Ser Glu Pro Glu Ile Gln Phe His Asn Val Lys Pro Gln Leu Pro
    210                 215                 220
Val Thr Pro Glu Asn Leu Ala Ala Ile Asp Leu Ile Arg Gln Arg Leu
225                 230                 235                 240
Ile Asn Glu Phe Val Gly Gly Glu Lys Glu Thr Asn Leu Ala Leu Glu
                245                 250                 255
Glu Asn Ile Ser Lys Leu Lys Ser Asp Phe Asp Ala Leu Asn Thr His
            260                 265                 270
Thr Leu Ala Asn Gly Gly Thr Gln Gly Arg His Leu Ile Thr Asp Lys
        275                 280                 285
Gln Ile Ile Ile Tyr Gln Pro Glu Asn Leu Asn Ser Gln Asp Lys Gln
    290                 295                 300
Leu Phe Asp Asn Tyr Val Ile Leu Gly Asn Tyr Thr Thr Leu Met Phe
305                 310                 315                 320
Asn Ile Ser Arg Ala Tyr Val Leu Glu Lys Asp Pro Thr Gln Lys Ala
                325                 330                 335
Gln Leu Lys Gln Met Tyr Leu Leu Met Thr Lys His Leu Leu Asp Gln
            340                 345                 350
Gly Phe Val Lys Gly Ser Ala Leu Val Thr Thr His His Trp Gly Tyr
        355                 360                 365
Ser Ser Arg Trp Trp Tyr Ile Ser Thr Leu Leu Met Ser Asp Ala Leu
    370                 375                 380
Lys Glu Ala Asn Leu Gln Thr Gln Val Tyr Asp Ser Leu Leu Trp Tyr
385                 390                 395                 400
Ser Arg Glu Phe Lys Ser Ser Phe Asp Met Lys Val Ser Ala Asp Ser
                405                 410                 415
Ser Asp Leu Asp Tyr Phe Asn Thr Leu Ser Arg Gln His Leu Ala Leu
            420                 425                 430
Leu Leu Leu Glu Pro Asp Asp Gln Lys Arg Ile Asn Leu Val Asn Thr
        435                 440                 445
Phe Ser His Tyr Ile Thr Gly Ala Leu Thr Gln Val Pro Pro Gly Gly
    450                 455                 460
Lys Asp Gly Leu Arg Pro Asp Gly Thr Ala Trp Arg His Glu Gly Asn
```

```
            465                 470                 475                 480
        Tyr Pro Gly Tyr Ser Phe Pro Ala Phe Lys Asn Ala Ser Gln Leu Ile
                        485                 490                 495
        Tyr Leu Leu Arg Asp Thr Pro Phe Ser Val Gly Glu Ser Gly Trp Asn
                    500                 505                 510
        Ser Leu Lys Lys Ala Met Val Ser Ala Trp Ile Tyr Ser Asn Pro Glu
                515                 520                 525
        Val Gly Leu Pro Leu Ala Gly Arg His Pro Leu Asn Ser Pro Ser Leu
            530                 535                 540
        Lys Ser Val Ala Gln Gly Tyr Tyr Trp Leu Ala Met Ser Ala Lys Ser
        545                 550                 555                 560
        Ser Pro Asp Lys Thr Leu Ala Ser Ile Tyr Leu Ala Ile Ser Asp Lys
                        565                 570                 575
        Thr Gln Asn Glu Ser Thr Ala Ile Phe Gly Glu Thr Ile Thr Pro Ala
                    580                 585                 590
        Ser Leu Pro Gln Gly Phe Tyr Ala Phe Asn Gly Gly Ala Phe Gly Ile
                595                 600                 605
        His Arg Trp Gln Asp Lys Met Val Thr Leu Lys Ala Tyr Asn Thr Asn
            610                 615                 620
        Val Trp Ser Ser Glu Ile Tyr Asn Lys Asp Asn Arg Tyr Gly Arg Tyr
        625                 630                 635                 640
        Gln Ile His Gly Val Ala Gln Ile Val Ser Asn Gly Ser Gln Leu Ser
                        645                 650                 655
        Gln Gly Tyr Gln Gln Glu Gly Trp Asp Trp Asn Arg Met Pro Gly Ala
                    660                 665                 670
        Thr Thr Ile His Leu Pro Leu Lys Asp Leu Asp Ser Pro Lys Pro His
                675                 680                 685
        Thr Leu Met Gln Arg Gly Glu Arg Gly Phe Ser Gly Thr Ser Ser Leu
            690                 695                 700
        Glu Gly Gln Tyr Gly Met Met Ala Phe Asp Leu Ile Tyr Pro Ala Asn
        705                 710                 715                 720
        Leu Glu Arg Phe Asp Pro Asn Phe Thr Ala Lys Lys Ser Val Leu Ala
                        725                 730                 735
        Ala Asp Asn His Leu Met Phe Ile Gly Ser Asn Ile Asn Ser Ser Asp
                    740                 745                 750
        Lys Asn Lys Asn Val Glu Thr Thr Leu Phe Gln His Ala Ile Thr Pro
                755                 760                 765
        Thr Leu Asn Thr Leu Trp Ile Asn Gly Gln Lys Ile Glu Asn Met Pro
            770                 775                 780
        Tyr Gln Thr Thr Leu Gln Gln Gly Asp Trp Leu Ile Asp Ser Asn Gly
        785                 790                 795                 800
        Asn Gly Tyr Leu Ile Thr Gln Ala Glu Lys Val Asn Val Ser Arg Gln
                        805                 810                 815
        His Gln Val Ser Ala Glu Asn Lys Asn Arg Gln Pro Thr Glu Gly Asn
                    820                 825                 830
        Phe Ser Ser Ala Trp Ile Asp His Ser Thr Arg Pro Lys Asp Ala Ser
                835                 840                 845
        Tyr Glu Tyr Met Val Phe Leu Asp Ala Thr Pro Glu Lys Met Gly Glu
            850                 855                 860
        Met Ala Gln Lys Phe Arg Glu Asn Asn Gly Leu Tyr Gln Val Leu Arg
        865                 870                 875                 880
        Lys Asp Lys Asp Val His Ile Ile Leu Asp Lys Leu Ser Asn Val Thr
                        885                 890                 895
```

```
Gly Tyr Ala Phe Tyr Gln Pro Ala Ser Ile Glu Asp Lys Trp Ile Lys
                900                 905                 910

Lys Val Asn Lys Pro Ala Ile Val Met Thr His Arg Gln Lys Asp Thr
            915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Ala Cys Arg Asp Ala Thr His Glu Arg Ala Pro
    995                 1000                1005

Glu Thr Ile Cys Ser Ile Asn Cys Cys Asn Phe Ile Asp Glu Asn
    1010                1015                1020

Thr Ile Ala Leu
    1025

<210> SEQ ID NO 3
<211> LENGTH: 1027
<212> TYPE: PRT
<213> ORGANISM: Artificial
<220> FEATURE:
<223> OTHER INFORMATION: Chondroitinase ABCI

<400> SEQUENCE: 3

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
```

```
                225                 230                 235                 240
Ile Asn Glu Phe Val Gly Gly Lys Glu Thr Asn Leu Ala Leu Glu
                245                 250                 255

Glu Asn Ile Ser Lys Leu Lys Ser Asp Phe Asp Ala Leu Asn Thr His
                260                 265                 270

Thr Leu Ala Asn Gly Gly Thr Gln Gly Arg His Leu Ile Thr Asp Lys
                275                 280                 285

Gln Ile Ile Ile Tyr Gln Pro Glu Asn Leu Asn Ser Gln Asp Lys Gln
                290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
                340                 345                 350

Gly Phe Val Lys Gly Ser Ala Leu Val Thr Thr His His Trp Gly Tyr
                355                 360                 365

Ser Ser Arg Trp Trp Tyr Ile Ser Thr Leu Leu Met Ser Asp Ala Leu
                370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
                420                 425                 430

Leu Leu Leu Glu Pro Asp Asp Gln Lys Arg Ile Asn Leu Val Asn Thr
                435                 440                 445

Phe Ser His Tyr Ile Thr Gly Ala Leu Thr Gln Val Pro Pro Gly Gly
                450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
                500                 505                 510

Ser Leu Lys Lys Ala Met Val Ser Ala Trp Ile Tyr Ser Asn Pro Glu
                515                 520                 525

Val Gly Leu Pro Leu Ala Gly Arg His Pro Leu Asn Ser Pro Ser Leu
                530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Thr Ile Thr Pro Ala
                580                 585                 590

Ser Leu Pro Gln Gly Phe Tyr Ala Phe Asn Gly Gly Ala Phe Gly Ile
                595                 600                 605

His Arg Trp Gln Asp Lys Met Val Thr Leu Lys Ala Tyr Asn Thr Asn
                610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655
```

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
675                 680                 685

Thr Leu Met Gln Arg Gly Glu Arg Gly Phe Ser Gly Thr Ser Ser Leu
690                 695                 700

Glu Gly Gln Tyr Gly Met Met Ala Phe Asp Leu Ile Tyr Pro Ala Lys
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Ala Cys Arg Asp Ala Thr His Glu Arg Ala Pro
        995                 1000                1005

Glu Thr Ile Cys Ser Ile Asn Cys Cys Asn Phe Ile Asp Glu Asn
        1010                1015                1020

Thr Ile Ala Leu
    1025

<210> SEQ ID NO 4
<211> LENGTH: 1027
<212> TYPE: PRT
<213> ORGANISM: Artificial
<220> FEATURE:
<223> OTHER INFORMATION: CHONDROITINASE ABCI

<400> SEQUENCE: 4

| | | | | | | | | | | | | | | |
|---|---|---|---|---|---|---|---|---|---|---|---|---|---|---|
|Ala|Thr|Ser|Asn|Pro|Ala|Phe|Asp|Pro|Lys|Asn|Leu|Met|Gln|Ser|Glu|
|1| | | |5| | | | |10| | | | |15| |

Ile Tyr His Phe Ala Gln Asn Asn Pro Leu Ala Asp Phe Ser Ser Asp
         20                  25                  30

Lys Asn Ser Ile Leu Thr Leu Ser Asp Lys Arg Ser Ile Met Gly Asn
         35                  40                  45

Gln Ser Leu Leu Trp Lys Trp Lys Gly Ser Ser Phe Thr Leu His
50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                 85                  90                  95

Ile Asp Gly Tyr Leu Thr Ile Asp Phe Gly Glu Lys Leu Ile Ser Thr
             100                 105                 110

Ser Glu Ala Gln Ala Gly Phe Lys Val Lys Leu Asp Phe Thr Gly Trp
         115                 120                 125

Arg Thr Val Gly Val Ser Leu Asn Asn Asp Leu Glu Asn Arg Glu Met
130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                 165                 170                 175

Ser Asn Val Ser Gln Gly Glu Ile Tyr Ile Asp Arg Ile Met Phe Ser
             180                 185                 190

Val Asp Asp Ala Arg Tyr Gln Trp Ser Asp Tyr Gln Val Lys Thr Arg
         195                 200                 205

Leu Ser Glu Pro Glu Ile Gln Phe His Asn Val Lys Pro Gln Leu Pro
210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                 245                 250                 255

Glu Asn Ile Ser Lys Leu Lys Ser Asp Phe Asp Ala Leu Asn Thr His
             260                 265                 270

Thr Leu Ala Asn Gly Gly Thr Gln Gly Arg His Leu Ile Thr Asp Lys
         275                 280                 285

Gln Ile Ile Ile Tyr Gln Pro Glu Asn Leu Asn Ser Gln Asp Lys Gln
290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                 325                 330                 335

Gln Leu Lys Gln Met Tyr Leu Leu Met Thr Lys His Leu Leu Asp Gln
             340                 345                 350

Gly Phe Val Lys Gly Ser Ala Leu Val Thr Thr His His Trp Gly Tyr
         355                 360                 365

Ser Ser Arg Trp Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Asn Ala Asp Ser
                 405                 410                 415

```
Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
            435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
            515                 520                 525

Val Gly Leu Pro Leu Ala Gly Arg His Pro Leu Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
    595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
    675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
            835                 840                 845
```

```
Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Ala Cys Arg Asp Ala Thr His Glu Arg Ala Pro
        995                 1000                1005

Glu Thr Ile Cys Ser Ile Asn Cys Cys Asn Phe Ile Asp Glu Asn
    1010                1015                1020

Thr Ile Ala Leu
    1025

<210> SEQ ID NO 5
<211> LENGTH: 1027
<212> TYPE: PRT
<213> ORGANISM: Artificial
<220> FEATURE:
<223> OTHER INFORMATION: CHONDROITINASE ABCI

<400> SEQUENCE: 5

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175
```

```
Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365

Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Glu Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
    530                 535                 540

Lys Ser Val Ala Gln Gly Tyr Tyr Trp Leu Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Glu Thr Ile Thr Pro Ala
            580                 585                 590

Ser Leu Pro Gln Gly Phe Tyr Ala Phe Asn Gly Gly Ala Phe Gly Ile
        595                 600                 605
```

```
His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
            645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
        690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
            755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
785                 790                 795                 800

Asn Gly Tyr Leu Ile Thr Gln Ala Glu Lys Val Asn Val Ser Arg Gln
                805                 810                 815

His Gln Val Ser Ala Glu Asn Lys Asn Arg Gln Pro Thr Glu Gly Asn
            820                 825                 830

Phe Ser Ser Ala Trp Ile Asp His Ser Thr Arg Pro Lys Asp Ala Ser
        835                 840                 845

Tyr Glu Tyr Met Val Phe Leu Asp Ala Thr Pro Glu Lys Met Gly Glu
    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                885                 890                 895

Gly Tyr Ala Phe Tyr Gln Pro Ala Ser Ile Glu Asp Lys Trp Ile Lys
            900                 905                 910

Lys Val Asn Lys Pro Ala Ile Val Met Thr His Arg Gln Lys Asp Thr
        915                 920                 925

Leu Ile Val Ser Ala Val Thr Pro Asp Leu Asn Met Thr Arg Gln Lys
    930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                965                 970                 975

Thr Glu Leu Thr Phe Thr Ser Tyr Phe Gly Ile Pro Gln Glu Ile Lys
            980                 985                 990

Leu Ser Pro Leu Pro Ala Cys Arg Asp Ala Thr His Glu Arg Ala Pro
        995                 1000                1005

Glu Thr Ile Cys Ser Ile Asn Cys Cys Asn Phe Ile Asp Glu Asn
    1010                1015                1020

Thr Ile Ala Leu
```

```
                                1025

<210> SEQ ID NO 6
<211> LENGTH: 1027
<212> TYPE: PRT
<213> ORGANISM: Artificial
<220> FEATURE:
<223> OTHER INFORMATION: CHONDROITINASE ABCI

<400> SEQUENCE: 6

Ala Thr Ser Asn Pro Ala Phe Asp Pro Lys Asn Leu Met Gln Ser Glu
  1               5                  10                  15

Ile Tyr His Phe Ala Gln Asn Asn Pro Leu Ala Asp Phe Ser Ser Asp
             20                  25                  30

Lys Asn Ser Ile Leu Thr Leu Ser Asp Lys Arg Ser Ile Met Gly Asn
         35                  40                  45

Gln Ser Leu Leu Trp Lys Trp Lys Gly Gly Ser Ser Phe Thr Leu His
     50                  55                  60

Lys Lys Leu Ile Val Pro Thr Asp Lys Glu Ala Ser Lys Ala Trp Gly
 65                  70                  75                  80

Arg Ser Ser Thr Pro Val Phe Ser Phe Trp Leu Tyr Asn Glu Lys Pro
                 85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
            180                 185                 190

Val Asp Asp Ala Arg Tyr Gln Trp Ser Asp Tyr Gln Val Lys Thr Arg
        195                 200                 205

Leu Ser Glu Pro Glu Ile Gln Phe His Asn Val Lys Pro Gln Leu Pro
    210                 215                 220

Val Thr Pro Glu Asn Leu Ala Ala Ile Asp Leu Ile Arg Gln Arg Leu
225                 230                 235                 240

Ile Asn Glu Phe Val Gly Gly Glu Lys Glu Thr Asn Leu Ala Leu Glu
                245                 250                 255

Glu Asn Ile Ser Lys Leu Lys Ser Asp Phe Asp Ala Leu Asn Thr His
            260                 265                 270

Thr Leu Ala Asn Gly Gly Thr Gln Gly Arg His Leu Ile Thr Asp Lys
        275                 280                 285

Gln Ile Ile Ile Tyr Gln Pro Glu Asn Leu Asn Ser Gln Asp Lys Gln
    290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
            340                 345                 350

Gly Phe Val Lys Gly Ser Ala Leu Val Thr Thr His His Trp Gly Tyr
        355                 360                 365
```

```
Ser Ser Arg Trp Trp Tyr Ile Ser Thr Leu Leu Met Ser Asp Ala Leu
    370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
            420                 425                 430

Leu Leu Leu Glu Pro Asp Asp Gln Lys Arg Ile Asn Leu Val Asn Thr
        435                 440                 445

Phe Ser His Tyr Ile Thr Gly Ala Leu Thr Gln Val Pro Pro Gly Gly
    450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
            500                 505                 510

Ser Leu Lys Lys Ala Met Val Ser Ala Trp Ile Tyr Ser Asn Pro Glu
        515                 520                 525

Val Gly Leu Pro Leu Ala Gly Arg His Pro Leu Asn Ser Pro Ser Leu
    530                 535                 540

Lys Ser Val Ala Gln Gly Tyr Tyr Trp His Ala Met Ser Ala Lys Ser
545                 550                 555                 560

Ser Pro Asp Lys Thr Leu Ala Ser Ile Tyr Leu Ala Ile Ser Asp Lys
                565                 570                 575

Thr Gln Asn Glu Ser Thr Ala Ile Phe Gly Thr Ile Thr Pro Ala
            580                 585                 590

Ser Leu Pro Gln Gly Phe Tyr Ala Phe Asn Gly Gly Ala Phe Gly Ile
        595                 600                 605

His Arg Trp Gln Asp Lys Met Val Thr Leu Lys Ala Tyr Asn Thr Asn
    610                 615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                645                 650                 655

Gln Gly Tyr Gln Gln Glu Gly Trp Asp Trp Asn Arg Met Pro Gly Ala
            660                 665                 670

Thr Thr Ile His Leu Pro Leu Lys Asp Leu Asp Ser Pro Lys Pro His
        675                 680                 685

Thr Leu Met Gln Arg Gly Glu Arg Gly Phe Ser Gly Thr Ser Ser Leu
    690                 695                 700

Glu Gly Gln Tyr Gly Met Met Ala Phe Asp Leu Ile Tyr Pro Ala Asn
705                 710                 715                 720

Leu Glu Arg Phe Asp Pro Asn Phe Thr Ala Lys Lys Ser Val Leu Ala
                725                 730                 735

Ala Asp Asn His Leu Ile Phe Ile Gly Ser Asn Ile Asn Ser Ser Asp
            740                 745                 750

Lys Asn Lys Asn Val Glu Thr Thr Leu Phe Gln His Ala Ile Thr Pro
        755                 760                 765

Thr Leu Asn Thr Leu Trp Ile Asn Gly Gln Lys Ile Glu Asn Met Pro
    770                 775                 780

Tyr Gln Thr Thr Leu Gln Gln Gly Asp Trp Leu Ile Asp Ser Asn Gly
```

```
                785                 790                 795                 800
Asn Gly Tyr Leu Ile Thr Gln Ala Glu Lys Val Asn Val Ser Arg Gln
                    805                 810                 815

His Gln Val Ser Ala Glu Asn Lys Asn Arg Gln Pro Thr Glu Gly Asn
                    820                 825                 830

Phe Ser Ser Ala Trp Ile Asp His Ser Thr Arg Pro Lys Asp Ala Ser
                    835                 840                 845

Tyr Glu Tyr Met Val Phe Leu Asp Ala Thr Pro Glu Lys Met Gly Glu
                    850                 855                 860

Met Ala Gln Lys Phe Arg Glu Asn Asn Gly Leu Tyr Gln Val Leu Arg
865                 870                 875                 880

Lys Asp Lys Asp Val His Ile Ile Leu Asp Lys Leu Ser Asn Val Thr
                    885                 890                 895

Gly Tyr Ala Phe Tyr Gln Pro Ala Ser Ile Glu Asp Lys Trp Ile Lys
                    900                 905                 910

Lys Val Asn Lys Pro Ala Ile Val Met Thr His Arg Gln Lys Asp Thr
                    915                 920                 925

Leu Ile Val Ser Ala Val Thr Pro Asp Leu Asn Met Thr Arg Gln Lys
            930                 935                 940

Ala Ala Thr Pro Val Thr Ile Asn Val Thr Ile Asn Gly Lys Trp Gln
945                 950                 955                 960

Ser Ala Asp Lys Asn Ser Glu Val Lys Tyr Gln Val Ser Gly Asp Asn
                    965                 970                 975

Thr Glu Leu Thr Phe Thr Ser Tyr Phe Gly Ile Pro Gln Glu Ile Lys
                    980                 985                 990

Leu Ser Pro Leu Pro Ala Cys Arg  Asp Ala Thr His Glu  Arg Ala Pro
                    995                  1000                1005

Glu Thr  Ile Cys Ser Ile Asn  Cys Cys Asn Phe Ile  Asp Glu Asn
     1010                 1015                1020

Thr Ile  Ala Leu
     1025

<210> SEQ ID NO 7
<211> LENGTH: 1027
<212> TYPE: PRT
<213> ORGANISM: Artificial
<220> FEATURE:
<223> OTHER INFORMATION: CHONDROITINASE ABCI

<400> SEQUENCE: 7

Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
                    20                  25                  30

Lys Asn Ser Ile Leu Thr Leu Ser Asp Lys Arg Ser Ile Met Gly Asn
            35                  40                  45

Gln Ser Leu Leu Trp Lys Trp Lys Gly Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                    85                  90                  95

Ile Asp Gly Tyr Leu Thr Ile Asp Phe Gly Glu Lys Leu Ile Ser Thr
                    100                 105                 110

Ser Glu Ala Gln Ala Gly Phe Lys Val Lys Leu Asp Phe Thr Gly Trp
            115                 120                 125
```

-continued

Arg Thr Val Gly Val Ser Leu Asn Asn Asp Leu Glu Asn Arg Glu Met
130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175

Ser Asn Val Ser Gln Gly Glu Ile Tyr Ile Asp Arg Ile Met Phe Ser
                180                 185                 190

Val Asp Asp Ala Arg Tyr Gln Trp Ser Asp Tyr Gln Val Lys Thr Arg
                195                 200                 205

Leu Ser Glu Pro Glu Ile Gln Phe His Asn Val Lys Pro Gln Leu Pro
210                 215                 220

Val Thr Pro Glu Asn Leu Ala Ala Ile Asp Leu Ile Arg Gln Arg Leu
225                 230                 235                 240

Ile Asn Glu Phe Val Gly Gly Lys Glu Thr Asn Leu Ala Leu Glu
                245                 250                 255

Glu Asn Ile Ser Lys Leu Lys Ser Asp Phe Asp Ala Leu Asn Thr His
                260                 265                 270

Thr Leu Ala Asn Gly Gly Thr Gln Gly Arg His Leu Ile Thr Asp Lys
                275                 280                 285

Gln Ile Ile Ile Tyr Gln Pro Glu Asn Leu Asn Ser Gln Asp Lys Gln
290                 295                 300

Leu Phe Asp Asn Tyr Val Ile Leu Gly Asn Tyr Thr Thr Leu Met Phe
305                 310                 315                 320

Asn Ile Ser Arg Ala Tyr Val Leu Glu Lys Asp Pro Thr Gln Lys Ala
                325                 330                 335

Gln Leu Lys Gln Met Tyr Leu Leu Met Thr Lys His Leu Leu Asp Gln
                340                 345                 350

Gly Phe Val Lys Gly Ser Ala Leu Val Thr Thr His His Trp Gly Tyr
                355                 360                 365

Ser Ser Arg Trp Trp Tyr Ile Ser Thr Leu Leu Met Ser Asp Ala Leu
370                 375                 380

Lys Glu Ala Asn Leu Gln Thr Gln Val Tyr Asp Ser Leu Leu Trp Tyr
385                 390                 395                 400

Ser Arg Glu Phe Lys Ser Ser Phe Asp Met Lys Val Ser Ala Asp Ser
                405                 410                 415

Ser Asp Leu Asp Tyr Phe Asn Thr Leu Ser Arg Gln His Leu Ala Leu
                420                 425                 430

Leu Leu Leu Glu Pro Asp Asp Gln Lys Arg Ile Asn Leu Val Asn Thr
                435                 440                 445

Phe Ser His Tyr Ile Thr Gly Ala Leu Thr Gln Val Pro Pro Gly Gly
                450                 455                 460

Lys Asp Gly Leu Arg Pro Asp Gly Thr Ala Trp Arg His Glu Gly Asn
465                 470                 475                 480

Tyr Pro Gly Tyr Ser Phe Pro Ala Phe Lys Asn Ala Ser Gln Leu Ile
                485                 490                 495

Tyr Leu Leu Arg Asp Thr Pro Phe Ser Val Gly Glu Ser Gly Trp Asn
                500                 505                 510

Ser Leu Lys Lys Ala Met Val Ser Ala Trp Ile Tyr Ser Asn Pro Glu
                515                 520                 525

Val Gly Leu Pro Leu Ala Gly Arg His Pro Leu Asn Ser Pro Ser Leu
530                 535                 540

Lys Ser Val Ala Gln Gly Tyr Tyr Trp Leu Ala Met Ser Ala Lys Ser

```
                545                 550                 555                 560
        Ser Pro Asp Lys Thr Leu Ala Ser Ile Tyr Leu Ala Ile Ser Asp Lys
                        565                 570                 575

Thr Gln Asn Glu Ser Thr Ala Ile Phe Gly Glu Thr Ile Thr Pro Ala
                        580                 585                 590

Ser Leu Pro Gln Gly Phe Tyr Ala Phe Asn Gly Gly Ala Phe Gly Ile
                        595                 600                 605

His Arg Trp Gln Asp Lys Met Val Thr Leu Lys Ala Tyr Asn Thr Asn
                        610                 615                 620

Val Trp Ser Ser Glu Ile Tyr Asn Lys Val Asn Arg Tyr Gly Arg Tyr
        625                 630                 635                 640

Gln Ser His Gly Val Ala Gln Ile Val Ser Asn Gly Ser Gln Leu Ser
                        645                 650                 655

Gln Gly Tyr Gln Gln Glu Gly Trp Asp Trp Asn Arg Met Pro Gly Ala
                        660                 665                 670

Thr Thr Ile His Leu Pro Leu Lys Asp Leu Asp Ser Pro Lys Pro His
                        675                 680                 685

Thr Leu Met Gln Arg Gly Glu Arg Gly Phe Ser Gly Thr Ser Ser Leu
                        690                 695                 700

Glu Gly Gln Tyr Gly Met Met Ala Phe Asp Leu Ile Tyr Pro Ala Asn
        705                 710                 715                 720

Leu Glu Arg Phe Asp Pro Asn Phe Thr Ala Lys Lys Ser Val Leu Ala
                        725                 730                 735

Ala Asp Asn His Leu Ile Phe Ile Gly Ser Asn Ile Asn Ser Ser Asp
                        740                 745                 750

Lys Asn Lys Asn Val Glu Thr Thr Leu Phe Gln His Ala Ile Thr Pro
                        755                 760                 765

Thr Leu Asn Thr Leu Trp Ile Asn Gly Gln Lys Ile Glu Asn Met Pro
                        770                 775                 780

Tyr Gln Thr Thr Leu Gln Gln Gly Asp Trp Leu Ile Asp Ser Asn Gly
        785                 790                 795                 800

Asn Gly Tyr Leu Ile Thr Gln Ala Glu Lys Val Asn Val Ser Arg Gln
                        805                 810                 815

His Gln Val Ser Ala Glu Asn Lys Asn Arg Gln Pro Thr Glu Gly Asn
                        820                 825                 830

Phe Ser Ala Trp Ile Asp His Ser Thr Arg Pro Lys Asp Ala Ser
                        835                 840                 845

Tyr Glu Tyr Met Val Phe Leu Asp Ala Thr Pro Glu Lys Met Gly Glu
                        850                 855                 860

Met Ala Gln Lys Phe Arg Glu Asn Asn Gly Leu Tyr Gln Val Leu Arg
        865                 870                 875                 880

Lys Asp Lys Asp Val His Ile Ile Leu Asp Lys Leu Ser Asn Val Thr
                        885                 890                 895

Gly Tyr Ala Phe Tyr Gln Pro Ala Ser Ile Glu Asp Lys Trp Ile Lys
                        900                 905                 910

Lys Val Asn Lys Pro Ala Ile Val Met Thr His Arg Gln Lys Asp Thr
                        915                 920                 925

Leu Ile Val Ser Ala Val Thr Pro Asp Leu Asn Met Thr Arg Gln Lys
                        930                 935                 940

Ala Ala Thr Pro Val Thr Ile Asn Val Thr Ile Asn Gly Lys Trp Gln
        945                 950                 955                 960

Ser Ala Asp Lys Asn Ser Glu Val Lys Tyr Gln Val Ser Gly Asp Asn
                        965                 970                 975
```

```
Thr Glu Leu Thr Phe Thr Ser Tyr Phe Gly Ile Pro Gln Glu Ile Lys
        980                 985                 990

Leu Ser Pro Leu Pro Ala Cys Arg Asp Ala Thr His Glu Arg Ala Pro
        995                 1000                1005

Glu Thr Ile Cys Ser Ile Asn Cys Cys Asn Phe Ile Asp Glu Asn
        1010                1015                1020

Thr Ile Ala Leu
        1025

<210> SEQ ID NO 8
<211> LENGTH: 2994
<212> TYPE: DNA
<213> ORGANISM: Proteus vulgaris

<400> SEQUENCE: 8
gccaccagca atcctgcatt tgatcctaaa aatctgatgc agtcagaaat ttaccatttt      60
gcacaaaata acccattagc agacttctca tcagataaaa actcaatact aacgttatct    120
gataaacgta gcattatggg aaaccaatct cttttatgga aatggaaagg tggtagtagc    180
tttactttac ataaaaaact gattgtcccc accgataaag aagcatctaa agcatgggga    240
cgctcatcca cccccgtttt ctcattttgg ctttacaatg aaaaaccgat tgatggttat    300
cttactatcg atttcggaga aaaactcatt tcaaccagtg aggctcaggc aggctttaaa    360
gtaaaattag atttcactgg ctggcgtact gtgggagtct ctttaaataa cgatcttgaa    420
aatcgagaga tgaccttaaa tgcaaccaat acctcctctg atggtactca agacagcatt    480
gggcgttctt taggtgctaa agtcgatagt attcgtttta aagcgccttc taatgtgagt    540
cagggtgaaa tctatatcga ccgtattatg ttttctgtcg atgatgctcg ctaccaatgg    600
tctgattatc aagtaaaaac tcgcttatca gaacctgaaa ttcaatttca caacgtaaag    660
ccacaactac ctgtaacacc tgaaaattta gcggccattg atcttattcg ccaacgtcta    720
attaatgaat tgtcggagg tgaaaaagag acaaacctcg cattagaaga gaatatcagc    780
aaattaaaaa gtgatttcga tgctcttaat actcacactt tagcaaatgg tggaacgcaa    840
ggcagacatc tgatcactga taaacaaatc attatttatc aaccagagaa tcttaactct    900
caagataaac aactatttga taattatgtt atttttaggta attacacgac attaatgttt    960
aatattagcc gtgcttatgt gctggaaaaa gatcccacac aaaaggcgca actaaagcag   1020
atgtacttat taatgacaaa gcatttatta gatcaaggct tgttaaagg gagtgctttta   1080 gtgacaaccc atcactgggg atacagttct cgttggtggt atatttccac gttattaatg   1140
tctgatgcac taaaagaagc gaacctacaa actcaagttt atgattcatt actgtggtat   1200
tcacgtgagt ttaaaagtag ttttgatatg aaagtaagtg ctgatagctc tgatctagat   1260
tatttcaata ccttatctcg ccaacattta gccttattac tactagagcc tgatgatcaa   1320
aagcgtatca acttagttaa tactttcagc cattatatca ctggcgcatt aacgcaagtg   1380
ccaccgggtg gtaaagatgg tttacgccct gatggtacag catggcgaca tgaaggcaac   1440
tatccgggct actctttccc agcctttaaa aatgcctctc agcttatttta tttattacgc   1500 gatacaccat tttcagtggg tgaaagtggt tggaatagcc tgaaaaaagc gatggtttca   1560
gcgtggatct acagtaatcc agaagttgga ttaccgcttg caggaagaca ccctcttaac   1620
tcaccttcgt taaaatcagt cgctcaaggc tattactggc ttgccatgtc tgcaaaatca   1680
tcgcctgata aaacacttgc atctatttat cttgcgatta gtgataaaac acaaaatgaa   1740
tcaactgcta tttttggaga aactattaca ccagcgtctt tacctcaagg tttctatgcc   1800
```

```
tttaatggcg gtgcttttgg tattcatcgt tggcaagata aaatggtgac actgaaagct    1860
tataacacca atgtttggtc atctgaaatt tataacaaag ataaccgtta tggccgttac    1920
caaagtcatg gtgtcgctca atagtgagt aatggctcgc agctttcaca gggctatcag    1980
caagaaggtt gggattggaa tagaatgcca ggggcaacca ctatccacct tcctcttaaa    2040
gacttagaca gtcctaaacc tcatacctta atgcaacgtg gagagcgtgg atttagcgga    2100
acatcatccc ttgaaggtca atatggcatg atggcattcg atcttattta tcccgccaat    2160
cttgagcgtt ttgatcctaa tttcactgcg aaaagagtg tattagccgc tgataatcac    2220 ttaatttta ttggtagcaa ataaatagt agtgataaaa ataaaaatgt tgaaacgacc    2280
ttattccaac atgccattac tccaacatta ataacccttt ggattaatgg acaaagata    2340 gaaaacatgc cttatcaaac aacacttcaa caaggtgatt ggttaattga tagcaatggc    2400
aatggttact taattactca agcagaaaaa gtaaatgtaa gtcgccaaca tcaggtttca    2460
gcggaaaata aaatcgcca accgacagaa ggaaacttta gctcggcatg gatcgatcac    2520
agcactcgcc ccaaagatgc cagttatgag tatatggtct ttttagatgc gacacctgaa    2580
aaaatgggag agatggcaca aaaattccgt gaaataatg ggttatatca ggttcttcgt    2640
aaggataaag acgttcatat tattctcgat aaactcagca atgtaacggg atatgccttt    2700
tatcagccag catcaattga agacaaatgg atcaaaaagg ttaataaacc tgcaattgtg    2760
atgactcatc gacaaaaaga cactcttatt gtcagtgcag ttacacctga tttaaatatg    2820
actcgccaaa aagcagcaac tcctgtcacc atcaatgtca cgattaatgg caaatggcaa    2880
tctgctgata aaatagtga agtgaaatat caggttctg gtgataacac tgaactgacg    2940
tttacgagtt actttggtat tccacaagaa atcaaactct cgccactccc ttga          2994
```

<210> SEQ ID NO 9
<211> LENGTH: 1027
<212> TYPE: PRT
<213> ORGANISM: Proteus vulgaris

<400> SEQUENCE: 9

```
Ala Thr Ser Asn Pro Ala Phe Asp Pro Lys Asn Leu Met Gln Ser Glu
1               5                   10                  15

Ile Tyr His Phe Ala Gln Asn Asn Pro Leu Ala Asp Phe Ser Ser Asp
            20                  25                  30

Lys Asn Ser Ile Leu Thr Leu Ser Asp Lys Arg Ser Ile Met Gly Asn
        35                  40                  45

Gln Ser Leu Leu Trp Lys Trp Lys Gly Ser Ser Phe Thr Leu His
    50                  55                  60

Lys Lys Leu Ile Val Pro Thr Asp Lys Glu Ala Ser Lys Ala Trp Gly
65                  70                  75                  80

Arg Ser Ser Thr Pro Val Phe Ser Phe Trp Leu Tyr Asn Glu Lys Pro
                85                  90                  95

Ile Asp Gly Tyr Leu Thr Ile Asp Phe Gly Glu Lys Leu Ile Ser Thr
            100                 105                 110

Ser Glu Ala Gln Ala Gly Phe Lys Val Lys Leu Asp Phe Thr Gly Trp
        115                 120                 125

Arg Thr Val Gly Val Ser Leu Asn Asn Asp Leu Glu Asn Arg Glu Met
    130                 135                 140

Thr Leu Asn Ala Thr Asn Thr Ser Ser Asp Gly Thr Gln Asp Ser Ile
145                 150                 155                 160

Gly Arg Ser Leu Gly Ala Lys Val Asp Ser Ile Arg Phe Lys Ala Pro
                165                 170                 175
```

```
Ser Asn Val Ser Gln Gly Glu Ile Tyr Ile Asp Arg Ile Met Phe Ser
            180                 185                 190
Val Asp Ala Arg Tyr Gln Trp Ser Asp Tyr Gln Val Lys Thr Arg
195                 200                 205
Leu Ser Glu Pro Glu Ile Gln Phe His Asn Val Lys Pro Gln Leu Pro
    210                 215                 220
Val Thr Pro Glu Asn Leu Ala Ala Ile Asp Leu Ile Arg Gln Arg Leu
225                 230                 235                 240
Ile Asn Glu Phe Val Gly Gly Glu Lys Glu Thr Asn Leu Ala Leu Glu
            245                 250                 255
Glu Asn Ile Ser Lys Leu Lys Ser Asp Phe Asp Ala Leu Asn Thr His
            260                 265                 270
Thr Leu Ala Asn Gly Gly Thr Gln Gly Arg His Leu Ile Thr Asp Lys
            275                 280                 285
Gln Ile Ile Ile Tyr Gln Pro Glu Asn Leu Asn Ser Gln Asp Lys Gln
290                 295                 300
Leu Phe Asp Asn Tyr Val Ile Leu Gly Asn Tyr Thr Thr Leu Met Phe
305                 310                 315                 320
Asn Ile Ser Arg Ala Tyr Val Leu Glu Lys Asp Pro Thr Gln Lys Ala
            325                 330                 335
Gln Leu Lys Gln Met Tyr Leu Leu Met Thr Lys His Leu Leu Asp Gln
            340                 345                 350
Gly Phe Val Lys Gly Ser Ala Leu Val Thr Thr His His Trp Gly Tyr
            355                 360                 365
Ser Ser Arg Trp Trp Tyr Ile Ser Thr Leu Leu Met Ser Asp Ala Leu
370                 375                 380
Lys Glu Ala Asn Leu Gln Thr Gln Val Tyr Asp Ser Leu Leu Trp Tyr
385                 390                 395                 400
Ser Arg Glu Phe Lys Ser Ser Phe Asp Met Lys Val Ser Ala Asp Ser
            405                 410                 415
Ser Asp Leu Asp Tyr Phe Asn Thr Leu Ser Arg Gln His Leu Ala Leu
            420                 425                 430
Leu Leu Leu Glu Pro Asp Asp Gln Lys Arg Ile Asn Leu Val Asn Thr
            435                 440                 445
Phe Ser His Tyr Ile Thr Gly Ala Leu Thr Gln Val Pro Pro Gly Gly
            450                 455                 460
Lys Asp Gly Leu Arg Pro Asp Gly Thr Ala Trp Arg His Glu Gly Asn
465                 470                 475                 480
Tyr Pro Gly Tyr Ser Phe Pro Ala Phe Lys Asn Ala Ser Gln Leu Ile
            485                 490                 495
Tyr Leu Leu Arg Asp Thr Pro Phe Ser Val Gly Glu Ser Gly Trp Asn
            500                 505                 510
Ser Leu Lys Lys Ala Met Val Ser Ala Trp Ile Tyr Ser Asn Pro Glu
            515                 520                 525
Val Gly Leu Pro Leu Ala Gly Arg His Pro Leu Asn Ser Pro Ser Leu
            530                 535                 540
Lys Ser Val Ala Gln Gly Tyr Tyr Trp Leu Ala Met Ser Ala Lys Ser
545                 550                 555                 560
Ser Pro Asp Lys Thr Leu Ala Ser Ile Tyr Leu Ala Ile Ser Asp Lys
            565                 570                 575
Thr Gln Asn Glu Ser Thr Ala Ile Phe Gly Glu Thr Ile Thr Pro Ala
            580                 585                 590
Ser Leu Pro Gln Gly Phe Tyr Ala Phe Asn Gly Gly Ala Phe Gly Ile
```

-continued

```
                595                 600                 605
His Arg Trp Gln Asp Lys Met Val Thr Leu Lys Ala Tyr Asn Thr Asn
610                         615                 620

Val Trp Ser Ser Glu Ile Tyr Asn Lys Asp Asn Arg Tyr Gly Arg Tyr
625                 630                 635                 640

Gln Ser His Gly Val Ala Gln Ile Val Ser Asn Gly Ser Gln Leu Ser
                        645                 650                 655

Gln Gly Tyr Gln Gln Glu Gly Trp Asp Trp Asn Arg Met Pro Gly Ala
                660                 665                 670

Thr Thr Ile His Leu Pro Leu Lys Asp Leu Asp Ser Pro Lys Pro His
                    675                 680                 685

Thr Leu Met Gln Arg Gly Glu Arg Gly Phe Ser Gly Thr Ser Ser Leu
690                         695                 700

Glu Gly Gln Tyr Gly Met Met Ala Phe Asp Leu Ile Tyr Pro Ala Asn
705                         710                 715                 720

Leu Glu Arg Phe Asp Pro Asn Phe Thr Ala Lys Lys Ser Val Leu Ala
                        725                 730                 735

Ala Asp Asn His Leu Ile Phe Ile Gly Ser Asn Ile Asn Ser Ser Asp
                    740                 745                 750

Lys Asn Lys Asn Val Glu Thr Thr Leu Phe Gln His Ala Ile Thr Pro
                755                 760                 765

Thr Leu Asn Thr Leu Trp Ile Asn Gly Gln Lys Ile Glu Asn Met Pro
770                         775                 780

Tyr Gln Thr Thr Leu Gln Gln Gly Asp Trp Leu Ile Asp Ser Asn Gly
785                         790                 795                 800

Asn Gly Tyr Leu Ile Thr Gln Ala Glu Lys Val Asn Val Ser Arg Gln
                        805                 810                 815

His Gln Val Ser Ala Glu Asn Lys Asn Arg Gln Pro Thr Glu Gly Asn
                    820                 825                 830

Phe Ser Ser Ala Trp Ile Asp His Ser Thr Arg Pro Lys Asp Ala Ser
                835                 840                 845

Tyr Glu Tyr Met Val Phe Leu Asp Ala Thr Pro Glu Lys Met Gly Glu
850                         855                 860

Met Ala Gln Lys Phe Arg Glu Asn Asn Gly Leu Tyr Gln Val Leu Arg
865                         870                 875                 880

Lys Asp Lys Asp Val His Ile Ile Leu Asp Lys Leu Ser Asn Val Thr
                        885                 890                 895

Gly Tyr Ala Phe Tyr Gln Pro Ala Ser Ile Glu Asp Lys Trp Ile Lys
                    900                 905                 910

Lys Val Asn Lys Pro Ala Ile Val Met Thr His Arg Gln Lys Asp Thr
                915                 920                 925

Leu Ile Val Ser Ala Val Thr Pro Asp Leu Asn Met Thr Arg Gln Lys
930                         935                 940

Ala Ala Thr Pro Val Thr Ile Asn Val Thr Ile Asn Gly Lys Trp Gln
945                         950                 955                 960

Ser Ala Asp Lys Asn Ser Glu Val Lys Tyr Gln Val Ser Gly Asp Asn
                        965                 970                 975

Thr Glu Leu Thr Phe Thr Ser Tyr Phe Gly Ile Pro Gln Glu Ile Lys
                    980                 985                 990

Leu Ser Pro Leu Pro Ala Cys Arg  Asp Ala Thr His Glu  Arg Ala Pro
                995                 1000                1005
```

```
Glu Thr Ile Cys Ser Ile Asn Cys Cys Asn Phe Ile Asp Glu Asn
    1010            1015            1020

Thr Ile Ala Leu
    1025
```

COMPOSITIONS AND METHODS OF USING CHONDROITINASE ABCI MUTANTS

CROSS-REFERENCE TO RELATED APPLICATIONS

This application is a continuation application of U.S. application Ser. No. 12/338,207, filed Dec. 18, 2008, now issued as U.S. Pat. No. 7,731,956, which is a divisional application of U.S. application Ser. No. 11/527,318 filed Sep. 26, 2006, now issued as U.S. Pat. No. 7,485,295 on Feb. 3, 2009, which claims priority from U.S. Application No. 60/720,628, filed Sep. 26, 2005; all applications are herein incorporated by reference in their entirety.

BACKGROUND

Proteoglycans, major constituents of the extracellular matrix, are known to be present in large amounts in glial scar tissue and to inhibit recovery following spinal cord injuries (Fawcett & Asher, 1999). Enzymes that are capable of digesting glial scar tissue are an important target for the development of spinal cord injury (SCI) therapeutics. Chondroitinase ABCI (EC 4.2.2.4; cABCI) is a bacterial enzyme that catalyzes the digestion of sulfated chondroitin and dermatan side chains of proteoglycans. This enzyme has been shown to promote functional recovery after spinal cord injury (Bradbury et al., 2002; Caggiano et al., 2005).

The spinal cord is made up of nerve fibers. Damage to the central nervous system, including the spinal cord, results in a loss of function. Depending upon the type of injury to the central nervous system, the loss of function may manifest itself in loss of sensory, motor or autonomic function or a combination thereof. Sensory functions include the ability to feel sensations, like pain. Motor functions include the ability to voluntarily move your body. Autonomic functions include involuntary body functions, for example the ability to sweat and breathe.

The most common types of spinal cord injuries (SCI) include contusions (bruising of the spinal cord) and compression injuries (caused by prolonged pressure on the spinal cord). In contusion and compression injuries, a cavity or hole often forms in the center of the spinal cord. Unlike nerve cells, or neurons of the peripheral nervous system (PNS), neurons of the central nervous system (CNS) do not regenerate after injury.

Spinal cord injury can be characterized by contusion of the neural tissue with a resultant decrease or loss of the ability of nerve tissue to properly transmit nerve impulses. The usual cause is due to an impact injury of some nature, but it may also occur during the manipulation of the spinal cord in certain surgical procedures. After a spinal cord injury in the adult mammal, the inability of axons to regenerate may lead to loss of sensation, loss of motor function and/or loss of autonomic function, as well as permanent paralysis. One reason that neurons fail to regenerate is their inability to traverse the glial scar that develops following a spinal cord injury. The injury-induced lesion will develop glial scarring, which contains extracellular matrix molecules including chondroitin sulfate proteoglycans (CSPGs). CSPGs inhibit nerve tissue growth in vitro and nerve tissue regeneration at CSPGs rich regions in vivo.

A number of molecules, and specified regions thereof, have been implicated in the ability to support the sprouting of neurites from a neuronal cell, a process also referred to as neurite outgrowth. The term neurite refers to both axon and dendrite structures. The process of sprouting neurites is essential in neural development and regeneration, especially after physical injury or disease has damaged neuronal cells. Neurites elongate profusely during development both in the central and peripheral nervous systems of all animal species. This phenomenon pertains to both axons and dendrites.

Various polypeptides, especially cell adhesion molecules (CAMs), have been known to promote neural cell growth. While early efforts in this area of research concentrated on the adhesion-promoting extracellular matrix protein fibronectin (FN), other polypeptides have also been found to promote neural growth. For example, U.S. Pat. No. 5,792,743 discloses novel polypeptides and methods for promoting neural growth in the CNS of a mammal by administering a soluble neural CAM, a fragment thereof, or a Fc-fusion product thereof. U.S. Pat. No. 6,313,265 discloses synthetic polypeptides containing the pharmacologically active regions of CAMs that can be used in promoting nerve regeneration and repair in both peripheral nerve injuries as well as lesions in the CNS. While helpful, the use of regenerative proteins alone may not be sufficient to effect repair of a damaged nervous system.

During approximately the past two decades, knowledge of cell adhesion and migration in extracellular matrices (ECMs) at the molecular level has expanded rapidly. The action of enzymes and other polypeptides which degrade components of the extracellular matrix and basement membranes may facilitate the events of neural repair by a variety of mechanisms, including the release of bound cytokines and by increasing the permeability of the matrix, thereby enhancing the mobility of mediator molecules, growth factors and chemotactic agents, as well as the cells involved in the healing process. For example, U.S. Pat. No. 5,997,863 discloses the use of glycosaminoglycans to manipulate cell proliferation and promote wound healing.

Components of the inhibitory CSPGs have been identified as the glycosaminoglycans, chondroitin sulfate (CS) and dermatan sulfate (DS). Removal of these inhibitory molecules would allow neurites to regenerate and reinnervate an area after physical injury or disease, as well as to allow for the recovery of sensory, motor and autonomic functions.

Previous studies have found that chondroitinases can lyse and degrade CSPGs including, CS and DS. One study found that chondroitinase ABC removed glycosaminoglycan (GAG) chains in and around lesioned areas of rat CNS in vivo. The degradation of GAGs promoted expression of a growth-associated protein, GAP-43, indicating an increase in the ability of treated cells to regenerate. However, this growth-associated protein is associated with regeneration in peripheral, but not central, nerve injuries.

Chondroitin sulfates (CS) are sulfated polysaccharides in linear chains of a repeated dissacharides. They range in molecular weight from about 10,000 to over 100,000 Da. Chondroitin sulfate substrates exist in different isomers designated by the appended letters A, B, and C (Hoffman et al., 1958). The repeating units are composed of uronic acid (GlcA or IdoA) and galactosamine, and are called galactosaminoglycans, and are one example of the glycosaminoglycans, typically abbreviated as GAG. Although these GAG chain species have different repeating disaccharide regions, they are covalently bound through the so-called linkage region tetrasaccharide sequence (see below) to the serine residue in the GAG attachment consensus sequence (Glu/Asp-X-Ser-Gly) of respective core proteins. Chondroitin A and C sulfates (ChS-A, ChS-C) are the most abundant GAGs and are found in cartilage, bone and heart valves. Chondroitin B (ChS-B, or, alternatively, dermatan sulfate) is expressed mostly in skin, blood vessels, and heart valves.

When chondroitinase bacterial preparations were characterized against different chondroitin sulfate (ChS) substrates, a series of distinct chondroitinases were discovered: Chondroitinase AC that degrades mostly chondroitin A (ChA) and chondroitin C (ChC) (Yamagata et al., 1968), Chondroitinase B that degrades chondroitin B (ChB) (Michelacci and Deitrich, 1976), Chondroitinase C that acts mostly on ChC (Michelacci Y M & Dietrich C P, 1976) and Chondroitinase ABC exhibits specificity against all three substrates—ChS-A, ChS-B and ChS-C (Yamagata et al., 1968, Michelacci et al., 1987).

SUMMARY OF THE INVENTION

One aspect of the present invention provides mutants of chondroitinase ABCI.

In preferred embodiments, such chondroitinase ABCI mutants exhibit enhanced activity. In other preferred embodiments, such chondroitinase ABCI mutants exhibit enhanced resistance to inactivation, including inactivation from UV or heat exposure. More preferably, the chondroitinase ABCI mutant enzymes are selected from BC6 (SEQ ID NO:1), BE7 (SEQ ID NO:2), BF4 (SEQ ID NO:3). In another preferred embodiment, the chondroitinase ABCI mutant enzymes are selected from BC9 (SEQ ID NO:4), BC7 (SEQ ID NO:5), RD4 (SEQ ID NO:6) and BE11 (SEQ ID NO: 7).

Another embodiment of the present invention is a method of designing mutants of chondroitinase ABCI having altered activity.

Other embodiments of the present invention relate to methods for promoting neurological functional recovery, including sensory, motor and autonomic function, after central nervous system ("CNS") injury or disease.

Further embodiments relate to methods of promoting neuronal outgrowth and the use in treating spinal cord injuries and related disorders of the CNS by administering such chondroitinase ABCI mutants.

DESCRIPTION OF THE DRAWINGS

In part, other aspects, features, benefits and advantages of the embodiments of the present invention will be apparent with regard to the following description, appended claims and accompanying drawings where:

DETAILED DESCRIPTION

Figure 1:
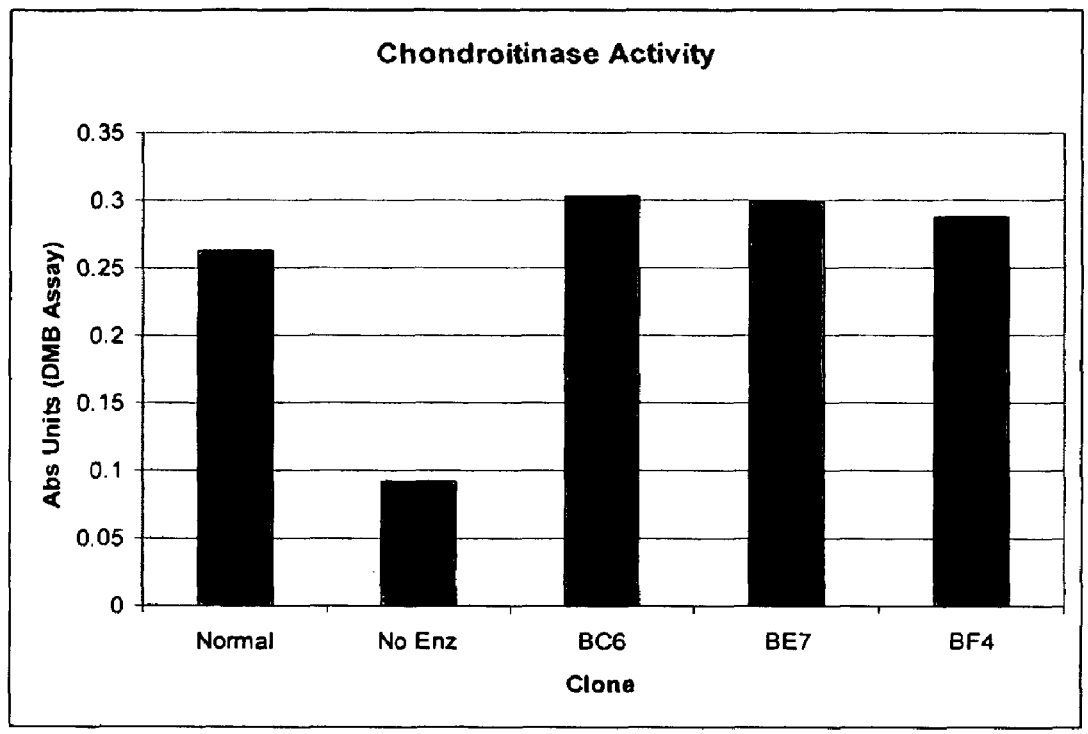
FIG. 1 is a bar graph of the chondroitin lyase activity of wild-type, not-inactivated chondroitinase ABCI (normal), wild-type, inactivated (No Enz) and chondroitinase ABCI mutant enzymes of the present invention following UV exposure.

Before the present compositions and methods are described, it is to be understood that this invention is not limited to the particular molecules, compositions, methodologies or protocols described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to a "cell" is a reference to one or more cells and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference. Nothing herein is to be construed as an admission that the invention is not entitled to antedate such disclosure by virtue of prior invention.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", can include, but is not limited to, providing an enzyme into the CNS or onto the target tissue; providing an enzyme systemically to a patient by, e.g., intravenous injection whereby the therapeutic reaches the target tissue; providing an enzyme in the form of the encoding sequence thereof to the target tissue (e.g., by so-called gene-therapy techniques). "Administering" a composition may be accomplished by injection, topical administration, or by either method in combination with other known techniques.

The term "animal" as used herein includes, but is not limited to, humans and non-human vertebrates such as wild, domestic and farm animals.

The term "improves" is used to convey that the present invention changes either the appearance, form, characteristics and/or the physical attributes of the target to which it is being provided, applied or administered. The change may be demonstrated by any of the following alone or in combination, including degradation of the CSPGs of the lesioned area of the spinal cord or within the CNS or restoring, in whole or in part, motor, sensory or autonomic function of the mammal.

The term "inhibiting" includes the administration of a compound of the present invention to prevent the onset of the symptoms, alleviating the symptoms, or eliminating the disease, condition or disorder.

By "pharmaceutically acceptable", it is meant the carrier, diluent or excipient must be compatible with the other ingredients of the formulation and not deleterious to the recipient thereof.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the protein. Moreover, the phrase "derived from", with respect to a recombinant gene, is meant to include within the meaning of "recombinant protein" those proteins having an amino acid sequence of a native protein, or an amino acid sequence similar thereto which is generated by mutations including substitutions and deletions (including truncation) of a naturally occurring form of the protein.

As used herein, the term "therapeutic" means an agent utilized to treat, combat, ameliorate, prevent or improve an unwanted condition or disease of a patient. In part, embodiments of the present invention are directed to the treatment of the central nervous system, such as degradation of the CSPGs of the lesioned area of the spinal cord or within the CNS or restoration, in whole or in part, motor, sensory or autonomic function of the mammal.

The terms "therapeutically effective amount" or "effective amount", as used herein, may be used interchangeably and refer to an amount of a therapeutic compound component of the present invention. For example, a therapeutically effective amount of a therapeutic compound is a predetermined amount calculated to achieve the desired effect, i.e., to effectively treat an injury to the central nervous system. For example, a therapeutic compound comprising a therapeutically effective amount of chondroitinase which may be purified by a method of the present invention and formulated to provide a stable, active enzyme, is sufficient to degrade the CSPGs of the lesioned area of the spinal cord or an amount sufficient to restore, in whole or in part, motor, sensory or autonomic function of the mammal and may result in a regeneration of neurons in a central nervous system, such as by promoting axonal growth into an injured area.

The terms "treat," "treated," or "treating" as used herein refers to both therapeutic treatment and prophylactic or preventative measures, wherein the object is to prevent or slow down (lessen) an undesired physiological condition, disorder or disease, or to obtain beneficial or desired clinical results. For the purposes of this invention, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term "vector" refers to a vehicle which can transport the nucleic acid molecules. The nucleic acid molecules encoding the chondroitinase polypeptide are covalently linked to the vector nucleic acid. With this aspect of the invention, the vector can be a plasmid, single or double stranded phage, a single or double stranded RNA or DNA viral vector, or artificial chromosome, such as a BAC, PAC, YAC, OR MAC.

Chondroitinase may be obtained from a microorganism that naturally expresses a chondroitinase; for example, but not limited to, *E. coli, Proteus vulgaris* or from the expression of a recombinant protein in a host cell. The host cell can be a prokaryotic cell (such as *E. coli*) or a eukaryotic cell (such as yeast, a mammalian cell or an insect cell).

The nucleotide sequence of chondroitinase ABCI is set forth as SEQ ID NO. 8 and the amino acid sequence of chondroitinase ABCI is set forth as SEQ ID NO. 9.

One aspect of the present invention provides mutants of chondroitinase ABCI. In a preferred embodiment, the chondroitinase ABCI mutant enzymes are selected from BC6 (SEQ ID NO:1), BE7 (SEQ ID NO:2), BF4 (SEQ ID NO:3). In another preferred embodiment, the chondroitinase ABCI mutant enzymes are selected from BC9 (SEQ ID NO:4), BC7 (SEQ ID NO:5), RD4 (SEQ ID NO:6) and BE11 (SEQ ID NO: 7).

Such enzymes may be formulated into pharmaceutical compositions and formulations. Suitable stable formulations and methods of purification are set forth in co-pending PCT Application No. US2005/017464 filed May 18, 2005 entitled "Methods of Purifying Chondroitinase and Stable Formulations Thereof" herein incorporated by reference in its entirety.

One aspect of the present invention provides mutants of chondroitinase ABCI. In preferred embodiments, such chondroitinase ABCI mutants exhibit enhanced activity.

In other preferred embodiments, such chondroitinase ABCI mutants exhibit enhanced resistance to inactivation. More preferably, the chondroitinase ABCI mutant enzymes are selected from BC6 (SEQ ID NO:1), BE7 (SEQ ID NO:2), BF4 (SEQ ID NO:3). In another preferred embodiment, the chondroitinase ABCI mutant enzymes are selected from BC9 (SEQ ID NO:4), BC7 (SEQ ID NO:5), RD4 (SEQ ID NO:6) and BE11 (SEQ ID NO: 7).

Another embodiment of the present invention is a method of designing mutants of chondroitinase ABCI having altered activity. The method comprises altering the nucleotide sequence or amino acid sequence of chondroitinase ABCI, expressing the chondroitinase ABCI in a suitable vector and measuring the activity of the mutant enzyme.

In a further embodiment, a stable chondroitinase ABCI enzyme is provided. The enzyme may exhibit increased resistance to inactivation under stressed conditions, including exposure to UV light or heat. In a preferred embodiment, the enzyme exhibits increased stability compared to wild-type chondroitinase ABCI enzyme following a challenge by a stress.

A further embodiment of the present invention is a method of treating central nervous system injuries comprising administering a chondroitinase ABCI mutant enzyme. In preferred embodiments, the chondroitinase ABCI mutant enzyme is administered in a therapeutically effective amount. In a preferred embodiment, the chondroitinase ABCI mutant enzyme is selected from the group consisting of BC6 (SEQ ID NO:1), BE7 (SEQ ID NO:2), BF4 (SEQ ID NO:3), BC9 (SEQ ID NO:4), BC7 (SEQ ID NO:5), RD4 (SEQ ID NO:6) and BE11 (SEQ ID NO: 7), more preferably, the enzyme is selected from the group consisting of BC6 (SEQ ID NO:1), BE7 (SEQ ID NO:2), and BF4 (SEQ ID NO:3). Such central nervous system injuries may include, but are not limited to, spinal cord injuries.

Another embodiment of the present invention is a method promoting neuronal outgrowth comprising administering a chondroitinase ABCI mutant enzyme. In preferred embodiments, the chondroitinase ABCI mutant enzyme is administered in a therapeutically effective amount. In a preferred embodiment, the chondroitinase ABCI mutant enzyme is selected from the group consisting of BC6 (SEQ ID NO:1), BE7 (SEQ ID NO:2), BF4 (SEQ ID NO:3), BC9 (SEQ ID NO:4), BC7 (SEQ ID NO:5), RD4 (SEQ ID NO:6) and BE11 (SEQ ID NO: 7), more preferably, the enzyme is selected from the group consisting of BC6 (SEQ ID NO:1), BE7 (SEQ ID NO:2), and BF4 (SEQ ID NO:3).

Other embodiments of the present invention relate to methods for promoting neurological functional recovery after central nervous system ("CNS") injury or disease. In preferred embodiments, the chondroitinase ABCI mutant enzyme is administered in a therapeutically effective amount. In particular, the present invention is directed to a method of utilizing chondroitinase to promote sensory, motor or autonomic neurological functional recovery following injury in or to the spinal cord. Compositions useful in this method include acceptable formulations of chondroitinase, more particularly sustained release formulations of chondroitinase. The present invention is also directed to a method of promoting neurological functional recovery after a contusion injury to the spinal cord. The most common types of spinal cord injuries (SCI) include contusions (bruising of the spinal cord) and compression injuries (caused by pressure on the spinal cord). In contusion injuries, the most common type of injury, a cavity or hole often forms in the center of the spinal cord.

The treatments of the present disclosure deliver an effective amount of the mutant or other optional therapeutic agent to the CNS or the injured site of the CNS. Such methods may include optionally administering other chondroitin sulfate proteoglycans, including, but not limited to chondroitinase $ABC_{Type1}$, chondroitinase $ABC_{Type11}$, chondroitinase AC and chondroitinase B or mammalian enzymes with chondroitinase-like activity such as Hyal1, Hyal2, Hyal3, and Hyal4, preferably to the CNS, and more preferably to the lesions of the injured area of the CNS.

As is known in the art, chondroitinase polypeptides can be produced by standard biological techniques or by chemical synthesis. For example, a host cell transfected with a nucleic acid vector directing expression of a nucleotide sequence encoding the subject polypeptides can be cultured under appropriate conditions to allow expression of the peptide to occur. The chondroitinase polypeptide may be secreted and isolated and from a mixture of cells and medium containing the recombinant chondroitinase polypeptide. Aspects of the invention described herein provide purification methods wherein the chondroitinase is isolated in a pure form that is more stable and active then those methods currently used.

Alternatively, the peptide may be retained cytoplasmically by removing the signal peptide sequence from the recombinant chondroitinase gene and the cells harvested, lysed and the protein isolated by the purification methods described herein.

Chondroitinase may be administered topically, locally or systemically. Topical or local administration is preferable for greater control of application. The chondroitinases, singularly or in combination, can be mixed with an appropriate pharmaceutical carrier prior to administration. Examples of generally used pharmaceutical carriers and additives are conventional diluents, binders, lubricants, coloring agents, disintegrating agents, buffer agents, isotonizing fatty acids, isotonizing agents, preservants, anesthetics, surfactants and the like, and are known to those skilled in the art. Specifically pharmaceutical carriers that may be used are dextran, sucrose, lactose, maltose, xylose, trehalose, mannitol, xylitol, sorbitol, inositol, serum albumin, gelatin, creatinine, polyethylene glycol, non-ionic surfactants (e.g. polyoxyethylene sorbitan fatty acid esters, polyoxyethylene hardened castor oil, sucrose fatty acid esters, polyoxyethylene polyoxypropylene glycol) and similar compounds. Pharmaceutical carriers may also be used in combination, such as polyethylene glycol and/or sucrose, or polyoxyethylene sorbitan fatty acid esters, polyoxyethylene sorbitan monooleate (20 E. 0.) is particularly preferred.

A treatment regimen according to the invention may be carried out by a means of administering a mutant chondroitinase ABCI enzyme of the present invention. The treatment regiment may further comprise administering chondroitinase ABCII, chondroitinase AC and chondroitinase B or mammalian enzymes with chondroitinase-like activity such as Hyal1, Hyal2, Hyal3, Hyal4 and PH2O to the lesions of the injured area of the CNS. The mode of administration, the timing of administration and the dosage are carried out such that the functional recovery from impairment of the CNS is enhanced by the promotion of neurite outgrowth.

The effective amount of chondroitinase can be administered in a single dosage, two dosages or a plurality of dosages. Although it is to be understood that the dosage may be administered at any time, in one embodiment, the dosage is administered within 12 hours after injury, or as soon as is feasible. In another embodiment, the dosage is administered to an injured mammal in one, two or a plurality of dosages; such dosages would be dependant on the severity of the injury and the amount of CSPGs present in the glial scarring. Where a plurality of dosages is administered, they may be delivered on a daily, weekly, or bi-weekly basis. The delivery of the dosages may be by means of catheter or syringe. Alternatively, the treatment can be administered during surgery to allow direct application to the glial scar.

For example, in some aspects, the invention is directed to a pharmaceutical composition comprising a compound, as defined above, and a pharmaceutically acceptable carrier or diluent, or an effective amount of a pharmaceutical composition comprising a compound as defined above.

The compounds of the present invention can be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the compounds of the present invention (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of compound to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

Pharmaceutical formulations containing the compounds of the present invention and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compounds of the present invention can be formulated for parenteral administration by injection, e.g., by bolus injection or continuous infusion. The compounds can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compounds can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid, or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The compounds of the present invention can also be formulated in rectal compositions such as suppositories or retention enemas, e.g., containing conventional suppository bases such as cocoa butter or other glycerides.

In addition to the formulations described previously, the compounds of the present invention can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the compounds of the present invention, for example, can be applied to a plaster, or can be applied by transdermal, therapeutic systems that are consequently supplied to the organism.

Pharmaceutical compositions of the compounds also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compounds of the present invention can also be administered in combination with other active ingredients, such as, for example, adjuvants, protease inhibitors, or other compatible drugs or compounds where such combination is seen to be desirable or advantageous in achieving the desired effects of the methods described herein.

The following methods are used to illustrate the various embodiments of the present invention. The methods are exemplary methods and are not meant to limit the invention.

Example 1

The present example illustrates exemplary chondroitinase mutant enzymes of the present invention. All nucleotide and amino acids are indicated as the wild-type and then the mutant version (Wild-type to Mutant).

| Mutant ABCI enzyme | Nucleotide sequence | Amino Acid sequence |
|---|---|---|
| BC6 (SEQ ID NO. 1) | T1206 to C1206 | E403 to G403 |
| | C1114 to A1114 | W372 to C372 |
| BE7 (SEQ ID NO. 2) | G1925 to T1925 | S642 to I642 |
| | T2226 to G2226 | I742 to M742 |
| BF4 (SEQ ID NO. 3) | T2160 to A2160 | N720 to K720e |
| BC9 (SEQ ID NO. 4) | G1238 to A1238 | S413 to N413 |
| BC7 (SEQ ID NO. 5) | A1468 to G1468 | K490 to E490 |
| RD4 (SEQ ID NO. 6) | T1661 to A1661 | L554 to H554 |
| BE11 (SEQ ID NO. 7) | A1901 to T1901 | D634 to V634 |
| | C1935 to T1935 (in wobble position of codon- does not result in AA change) | |

Example 2

The present example illustrates the chondroitin lyase activity of exemplary chondroitinase ABCI mutants according to the present invention following UV exposure. Mutant chondroitinase ABIC genes were generated and transformed into bacteria. Bacteria were grown and the mutagenized chondroitinase expressed. The chondroitinase were then exposed to UV light and their chondroitin lyase activity measured. As depicted in FIG. 1, clone BC6 (SEQ ID NO:1), BE7 (SEQ ID NO:2) and BF4 (SEQ ID NO:3) exhibited greater chondroitin lyase activity following exposure to UV light as compared to control.

Example 3

Figure 2:
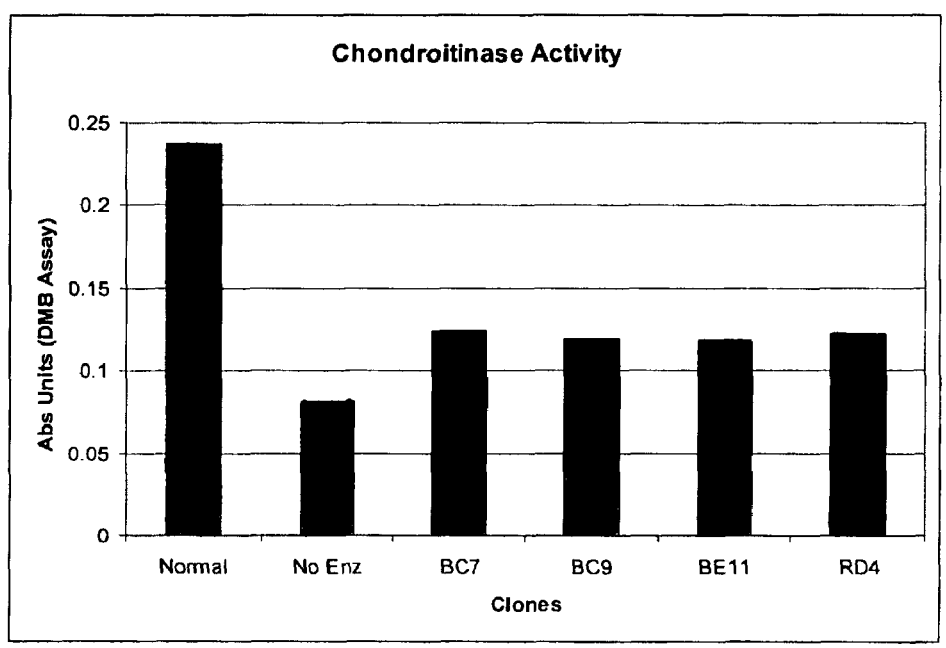
FIG. 2 is a bar graph of the chondroitin lyase activity of wild-type, not-inactivated chondroitinase ABCI (normal), wild-type, inactivated (No Enz) and chondroitinase ABCI mutant enzymes of the present invention.

The present example illustrates the chondroitin lyase activity of exemplary chondroitinase ABCI mutants according to the present invention. The chondroitinase lyase activity of Clone BC9, Clone BC7, Clone RD4 and Clone BE11 under normal (i.e., non-stressed) conditions was measured and exhibited decreased activity as compared to control an wild-type chondroitinase ABCI, as depicted in FIG. 2.

Although the present invention has been described in considerable detail with reference to certain preferred embodiments thereof, other versions are possible. Therefore the spirit and scope of the appended claims should not be limited to the description and the preferred versions contained within this specification.

---

What is claimed is:

1. An isolated mutant chondroitinase ABCI enzyme comprising the amino acid sequence of SEQ ID NO: 3.

2. A method of treating a central nervous system injury comprising administering a therapeutically effective amount of an isolated mutant chondroitinase ABCI enzyme comprising the amino acid sequence of SEQ ID NO: 3.

3. The method of claim 2, wherein the enzyme is administered following a contusion injury to the central nervous system.

4. The method of claim 2, wherein the enzyme is administered following a non-contusion injury to the central nervous system.

5. The method of claim 2, wherein the enzyme is administered following a spinal cord injury.

6. The method of claim 2, wherein the enzyme is administered locally.

7. The method of claim 6, wherein the local administration is selected from intrathecal and topical administration.

8. A method of promoting neuronal outgrowth comprising administering a therapeutically effective amount of an isolated mutant chondroitinase ABCI enzyme comprising the amino acid sequence of SEQ ID NO: 3.

9. The method of claim 8, wherein the enzyme is administered following a contusion injury to the central nervous system.

10. The method of claim 8, wherein the enzyme is administered following a non-contusion injury to the central nervous system.

11. The method of claim 8, wherein the enzyme is administered following a spinal cord injury.

12. The method of claim 8, wherein the enzyme is administered locally.

13. The method of claim 12, wherein the local administration is selected from intrathecal and topical administration.

* * * * *